(12) United States Patent
Itabashi et al.

(10) Patent No.: US 11,181,502 B2
(45) Date of Patent: Nov. 23, 2021

(54) HOLE FORMATION METHOD AND MEASUREMENT DEVICE

(71) Applicant: Hitachi High-Technologies Corporation, Tokyo (JP)

(72) Inventors: Naoshi Itabashi, Tokyo (JP); Sonoko Migitaka, Tokyo (JP); Itaru Yanagi, Tokyo (JP); Rena Akahori, Tokyo (JP); Kenichi Takeda, Tokyo (JP)

(73) Assignee: Hitachi High-Tech Corporation, Tokyo (JP)

( * ) Notice: Subject to any disclaimer, the term of this patent is extended or adjusted under 35 U.S.C. 154(b) by 0 days.

(21) Appl. No.: 15/129,854

(22) PCT Filed: Mar. 26, 2015

(86) PCT No.: PCT/JP2015/059424
§ 371 (c)(1),
(2) Date: Sep. 28, 2016

(87) PCT Pub. No.: WO2015/152003
PCT Pub. Date: Oct. 8, 2015

(65) Prior Publication Data
US 2017/0138899 A1    May 18, 2017

(30) Foreign Application Priority Data
Apr. 2, 2014   (JP) .............................. JP2014-075880

(51) Int. Cl.
*G01N 21/63* (2006.01)
*G01N 27/00* (2006.01)
(Continued)

(52) U.S. Cl.
CPC ..... *G01N 27/44721* (2013.01); *G01N 21/648* (2013.01); *G01N 21/6486* (2013.01);
(Continued)

(58) Field of Classification Search
CPC ........ B01D 17/00; B01D 67/00; B29C 35/68; B28C 65/00; H05B 6/00; C25F 3/00;
(Continued)

(56) References Cited

U.S. PATENT DOCUMENTS

2007/0172386 A1* 7/2007 Li ..................... G01N 33/48721
422/68.1
2011/0249259 A1  10/2011 Van Dorpe et al.
(Continued)

FOREIGN PATENT DOCUMENTS

JP     2006-523144 A    10/2006
JP     2013-90576 A      5/2013
(Continued)

OTHER PUBLICATIONS

Bouhelier A., et al., "Electrolytic formation of nanoapertures for scanning near-field optical microscopy", Jul. 30, 2001, Applied Physics Letters, vol. 79, No. 5. (Year: 2001).*
(Continued)

*Primary Examiner* — Edna Wong
(74) *Attorney, Agent, or Firm* — Crowell & Moring LLP

(57) ABSTRACT

While an insulating film having a near-field light generating element placed thereon is being irradiated with light in an electrolytic solution, or after the film that has been irradiated with light is disposed in the electrolytic solution, a first voltage is applied between the two electrodes installed in the electrolytic solution across the film, a second voltage is then applied between the two electrodes, and a value of a current that flows between the two electrodes due to the application of the second voltage is detected. This procedure is stopped when the current value reaches or exceeds a pre-set threshold value, whereby a hole is formed at a desired location in the thin-film.

3 Claims, 23 Drawing Sheets

(51) Int. Cl.
*G01N 27/92* (2006.01)
*G01N 27/447* (2006.01)
*G01N 21/64* (2006.01)
*G01N 21/65* (2006.01)
*G01N 33/487* (2006.01)
*B82Y 40/00* (2011.01)

(52) U.S. Cl.
CPC ..... *G01N 21/658* (2013.01); *G01N 27/44791* (2013.01); *G01N 33/48721* (2013.01); *B82Y 40/00* (2013.01)

(58) Field of Classification Search
CPC ........ C25F 3/12; G01N 21/63; G01N 21/648; G01N 21/658; G01N 27/00; G01N 27/92
USPC ................. 264/42, 400, 405, 482, 483, 485; 205/766, 644; 430/296; 702/64
See application file for complete search history.

(56) References Cited

U.S. PATENT DOCUMENTS

| | | | |
|---|---|---|---|
| 2013/0176563 A1 | 7/2013 | Ozawa et al. | |
| 2014/0262820 A1* | 9/2014 | Kuan | B01D 67/0034 205/665 |
| 2016/0033471 A1* | 2/2016 | Meller | G01N 33/48721 435/6.1 |

FOREIGN PATENT DOCUMENTS

| | | | | |
|---|---|---|---|---|
| WO | WO 2004/077503 A2 | 9/2004 | | |
| WO | WO 2012/043028 A1 | 4/2012 | | |
| WO | WO 2013/167952 A1 | 11/2013 | | |
| WO | WO 2013/167955 A1 | 11/2013 | | |
| WO | WO-2013167952 A1 * | 11/2013 | ............. | G01N 33/00 |

OTHER PUBLICATIONS

Bouhelier et al., "Electrolytic Formation of Nanoapertures for Scanning Near-Field Optical Microscopy," Applied Physics Letters (Jul. 30, 2001), vol. 79, No. 5, pp. 683-685. (Year: 2001).*
Kwok et al., "Nanopore Fabrication by Controlled Dielectric Breakdown," Plos One (Mar. 2014), vol. 9, Issue 3, pp. 1-6. (Year: 2014).*
Jonsson et al., "Plasmonic Nanopore for Electrical Profiling of Optical Intensity Landscapes," Nano Lett. (2013), vol. 13, pp. 1029-1033. (Year: 2013).*
Kwok et al., "Nanopore Fabrication by Controlled Dielectric Breakdown," PloS one (Mar. 21, 2014), vol. 9, No. 3, pp. 1-6. (Year: 2014).*
Lo et al., "Near-Field Photolithography by a Fiber Probe," In Proceedings of the 2001 1st IEEE Conference on Nanotechnology. IEEE-NANO 2001 (Cat. No. 01EX516) [Oct. 30, 2001], pp. 36-39). IEEE. (Year: 2001).*
International Search Report (PCT/ISA/210) issued in PCT Application No. PCT/JP2015/059424 dated Jun. 23, 2015 with English translation (Four (4) pages).
Japanese-language Written Opinion (PCT/ISA/237) issued in PCT Application No. PCT/JP2015/059424 dated Jun. 23, 2015 (Three (3) pages).
Rosenstein, J. K., et al., "Integrated Nanopore Sensing Platform with Sub-Microsecond Temporal Resolution", Nature Methods, May 2012, vol. 9, No. 5, pp. 487-492 plus Online Methods doi: 10.1038/nmeth. 1932 (Eight (8) pages).
Kwok, H., et al., "Nanopore Fabrication by Controlled Dielectric Breakdown", Plos One, Mar. 2014, vol. 9, Issue 3, e92880 (Six (6) pages).
German-language Office Action issued in counterpart German Application No. 11 2015 001 642.2 dated Jun. 12, 2019 (10 pages).

* cited by examiner

Electrode pair array for tunnel current measurement

Wiring

FIG. 19

| Item | Condition | A | B | C | D | E |
|---|---|---|---|---|---|---|
| Hole opening | Light irradiation | OFF | OFF | ON | ON (Higher output) | ON (Shorter wavelength) (Higher energy) |
| | Voltage | 4V | 4V | 4V | 2V | 2V |
| | Hole formation | Good | Good | Good | Good | Good |
| | Hole position | Poor | Poor | Good | Good | Good |
| Hole diameter measurement | Voltage | 4V | 1V | 1V | 2V | 2V |
| | Light irradiation | OFF | OFF | OFF | OFF | OFF |
| | Hole enlargement | Yes | No | No | No | No |
| Overall evaluation | | Poor | Poor | Good | Good | Good |

HOLE FORMATION METHOD AND MEASUREMENT DEVICE

TECHNICAL FIELD

The present invention relates to a nanopore technology for measuring biomolecules, or DNA in particular.

BACKGROUND ART

Non Patent Literature 1 discloses a nanopore formation method including irradiating a membrane of a silicon nitride film ($Si_3N_4$) or the like with an electron beam with a narrowed diameter using a transmission electron microscope (TEM) device, and controlling energy and current so as to form a pore with a diameter of not greater than 10 nm.

In Non Patent Literature 2, another nanopore formation method is disclosed. In this method, a membrane ($Si_3N_4$ film) with a thickness of 10 nm and having no hole is placed in a chamber filled with an aqueous solution (potassium chloride) above and below the membrane; electrodes are immersed in the KCl aqueous solution respectively in the upper and lower regions of the chamber; and a voltage is continuously applied between the electrodes. The application of voltage is stopped when a current in a direction penetrating through the membrane exceeds a certain current threshold value. As shown by FIG. 2f in Non Patent Literature 2, 5 V is continuously applied between the electrodes, and the voltage application is stopped when the inter-electrode current reaches the current threshold value between 400 s and 500 s, whereby a nanopore with a hole diameter on the order of 5 nm is formed.

CITATION LIST

Non Patent Literature

Non Patent Literature 1: Jacob K Rosenstein, et al., "*Integrated nanopore sensing platform with sub-microsecond temporal resolution*", Nature Methods, Vol. 9, No. 5, 487-492 (2012)

Non Patent Literature 2: Kwok, H., Briggs, K., and Tabard-Cossa, V., "*Nanopore Fabrication by Controlled Dielectric Breakdown*", PLOS ONE, Vol. 9, Issue 3, e92880 (2014)

SUMMARY OF INVENTION

Technical Problem

According to a measurement technology using a nanopore, a nanometer-level hole (nanopore 103) of approximately the same order as the thickness of a DNA molecule 102 is provided in a region 101 of a thin-film membrane, a chamber 104 is filled with an aqueous solution 105 above and below the thin-film membrane, the DNA 102 to be measured is put in either upper or lower regions of the chamber, and a measurement is made as the DNA passes through the nanopore, so as to determine structural features or the base sequence of the DNA (FIG. 1). The methods for making the measurement when the DNA passes through the nanopore include an optical measurement method (by which a light signal 109 is measured through light excitation 108) and an electrical measurement method (by which an electrical signal 110 is measured).

An analysis of nanopore formation, for use in optical measurement and tunnel current measurement in particular, by means of the hole opening method using the TEM device according to Non Patent Literature 1 and by the hole opening method based on voltage application according to Non Patent Literature 2 has identified problems, as will be described below.

For optical measurement using a nanopore, by one method, light excitation is caused when a molecule passes through the nanopore, and light emission from the excited molecule or from an excited marker attached to the molecule is measured. As a means for measuring the light, a device is provided with a plasmon enhancement structure that generates near-field light in close proximity to the nanopore location. Examples of the plasmon enhancement structure include one in which a conductor thin-film 402 is formed on an insulating film membrane 401 and provided with holes 403 (a hole array); a bow-tie 404 (bow-tie array) in which two conductor dots are disposed close to each other; and one in which two conductor dots 406 are stacked vertically, with a gap therebetween insulated with an insulator thin-film 407 (double-stack dot array) (FIG. 4). When the device is irradiated with light, a near-field light generated position 408 is at the center position in the bottom of the hole 403 in the hole structure, at the position of a gap 405 between the two conductor dots in the bow-tie structure, or at the gap at 407 of the dot structure in the double-stack dot array, and the near-field light can be used as excitation light for optical measurement.

In an example of hole formation, a test was conducted to open a hole with a hole diameter of 5 nm using the TEM device aiming at the gap position (gap center point) between the two conductor dots of the bow-tie structure on a membrane. This position is where near-field light is generated during measurement. However, when the same hole opening was attempted a plurality of times and the finished size was examined, it was learned that there was hole diameter variations on the order of 2 nm at 3σ with respect to the target hole diameter of 5 nm. Also, when an operation was performed to accurately form a hole at the center point position of the bow-tie gap using a position adjustment mechanism of the TEM device, the operation failed to open the hole at the center point position of the gap accurately. When the hole opening operation was performed a plurality of times, misalignment (positional variations) on the order of 5 nm at 3σ from the target position was caused.

Thereafter, the devices that had hole diameter or hole position variations due to the hole formation using the TEM device were successively loaded in an evaluation chamber, into which an aqueous solution containing DNA was injected and irradiated with excitation light to measure the strength of light signals emitted when the DNA passed through the nanopore. As a result, it was learned that there were very large variations in the strength of the light signals emitted from the DNA due to the individual devices, and that there was a difference of two or more orders of magnitude between the strongest light signal and the weakest light signal. The near-field light generated by plasmon enhancement becomes stronger locally. For example, in the bow-tie structure, when the gap interval is 5 nm, the near-field light becomes strong locally only in the 5 nm region of the gap. Accordingly, if the hole expands so much that the position at which the DNA molecule passes through the hole cannot be determined, or if the hole position is displaced from the center point position of the gap, the excitation light to which the molecule is subjected becomes weak, inevitably resulting in a significant decrease in light signal. In principle, it may be thought that the influence on the decrease in strength will be greater when the hole position itself is displaced than when the hole diameter increases so much that the DNA passage position cannot be determined. However, even when the position is accurate, other adverse influences could be present, such as when the hole diameter expands (to 7 nm, for example) while also the tip-end portions of the bow-tie are shaved off, causing the gap to increase (from the original 5 nm to 7 nm), and resulting in a decrease in light signal strength. In any case, the resultant signal strength could be totally varied by variations of a mere several nm in hole diameter or hole position. Thus, it has been difficult to reproducibly manufacture nanopore devices for the optical measurement system with uniform performance, by the hole opening process using TEM.

Another representative example of the device for measuring a molecule that is passed through a nanopore by providing a structure near the nanopore is a tunnel current measurement system. The tunnel current measurement system includes pairs of tunnel current measuring electrodes 501 disposed on the plane of an insulating film membrane (FIG. 5(a)), with a hole provided in a gap 502 between the tip-end portions of the electrode pairs, where a tunnel current that flows through a DNA molecule as the DNA molecule passes through the hole is measured while a voltage is applied between the electrodes. The system may be considered similar to the above-described bow-tie configuration in that a hole is opened aiming at the gap between a pair of conductor structures, while differing in that in the device, electric wiring 503 is provided for each of the two dots of the bow-tie, for example, the electric wiring being connected to a power supply and used for measurement (FIG. 5(b)).

As in the case of the bow-tie, an attempt was made several times to open a hole with a hole diameter of 5 nm aiming at the gap position 502 (gap center point) between a pair of conductor structures, using the TEM device. However, as in the case of the bow-tie, there were hole diameter variations on the order of 2 nm at 3σ with respect to the target of 5 nm, and there was also a hole position misalignment (positional variation) on the order of 5 nm at 3σ from the target gap center point position.

The performance of a tunnel current system nanopore device having such hole diameter and hole position variations was evaluated. As a result, it was learned that the tunnel current system similarly had very large measurement performance variations. In those chips in which the hole happened to be formed at exactly the gap center point, the tunnel current was able to be measured with high accuracy. However, in the chips that had a hole diameter increase of 2 nm or a hole position displacement of 2 nm, the tunnel current change due to the passing of DNA molecule through the nanopore was greatly decreased below a detection limit, so that significant signal confirmation was impossible. The tunnel current change at the time of passing of DNA molecule through a nanopore becomes rapidly weak if the DNA molecule is displaced even a little from a current path connecting the electrode pair disposed in close vicinity to the nanopore. The tunnel current change also becomes rapidly weak as the hole becomes larger and the gap expands when the tip-end portions of the electrodes on both sides in close vicinity to the hole are shaved. Accordingly, it is considered that in the fabrication of the nanopore device used for the tunnel current measurement system, too, the signal strength obtained by subsequent measurements was varied totally just because the hole diameter or hole position had been varied by mere several nanometers.

Thus, with respect to the nanopore devices corresponding to any of the measurement systems, the hole opening method using the TEM device was unable to achieve sufficient processing accuracy for measurement applications. In addition, the method using the TEM device has the problem not only of accuracy but also high device cost and low throughput.

Accordingly, with the expectation of improvements in accuracy, device cost, and throughput, the hole opening method according to Non Patent Literature 2 was next tested. It was expected that this method, as long as sufficient hole opening performance could be obtained, would greatly improve throughput compared with the method using the TEM device, because the required power supply device is inexpensive and no vacuum system is employed.

As in the above-described hole opening processing using the TEM device, a membrane ($Si_3N_4$ film) with a thickness of 10 nm and having no hole was prepared; upper and lower chambers across the membrane were filled with a potassium chloride aqueous solution (KCl aqueous solution); the electrodes were respectively immersed in the KCl aqueous solution in the upper and lower portions of the chamber; and a voltage was applied between the electrodes (FIG. 2). The voltage was continuously applied while monitoring the transition of the current between the electrodes, and the process was stopped at 440 seconds when the current value exceeded a threshold value. As a result, in the initial round, a nanopore having a hole diameter of 5 nm was formed at a position which was displaced by approximately 40 nm from the center of the membrane region to the left. A plurality of membranes having no hole was further prepared and the hole opening was successively implemented under identical condition settings, and the variations in the finished size of the holes were examined. As a result, there were hole diameter variations on the order of 1 nm at 3σ with respect to the target hole diameter of 5 nm. It was thus learned that, while the variations suppressed down to 1 nm were not yet sufficient, the method according to Non Patent Literature 2 was at least able to improve the hole diameter variations, compared with the hole opening using the TEM device.

However, with regard to the position of a hole, as indicated in Non Patent Literature 2, it was not possible to easily form a hole at the position at around the center of the flat membrane having no characteristic structures disposed thereon. In the second round (second chip), a hole was formed at a position displaced by 35 nm from the membrane center toward upper right; in the third round, a hole was formed at a position close to the center; in the fourth round, a hole was formed at a position at a distance of 45 nm from the center position diagonally toward lower right. Accordingly, the method whereby the hole was opened by voltage application with the upper/lower regions of the chamber filled with an aqueous solution has the advantage of reduced hole diameter variations and higher accuracy compared with the method using the TEM device; however, the hole position is not definite.

Next, with respect to a device in which the structure (bow-tie or an electrode pair) used for the optical measurement system or the tunnel current measurement system was disposed on a membrane, hole opening by the method according to Non Patent Literature 2 was analyzed. As described above, the nanopore used for the optical measurement system or the tunnel current system needs to be formed at the position of the bow-tie gap or the position of the electrode pair gap. Hole opening was implemented by: fabricating a device in which the bow-tie 404 for the optical measurement system was formed at the center of the membrane region 101 with a thickness of 10 nm, and a device in which the electrode pair gap structure for the tunnel current measurement system was formed; loading the devices in the chamber 104; injecting the aqueous solution 105; and applying a voltage. Because a plasmon enhancement device such as the bow-tie is an element that enhances near-field light, there may be some optical influence during an experiment conducted in a bright location. Accordingly, during the analysis of the hole opening processing with respect to the bow-tie and the electrode pair, the hole opening experiments were implemented in a darkroom (shielding box) so that the effect of voltage application could be confirmed while eliminating optical influences.

Nevertheless, despite the presence of conductor structures such as the bow-ties or electrode pairs on the plane of the membrane, no particular tendency was observed of a hole being opened at a position in close proximity to the characteristic features, such as in the vicinity of the structure edge or the gap portion, and the nanopore 103 with a hole diameter of 5 nm was accurately formed at a random location having no relationship with the location of the structures. No influence of the structures formed on the membrane on the position of hole formation was observed (FIG. 6).

Thus, the bow-tie structure used for the optical measurement system and the electrode pair used for the tunnel current system were formed on the surface of the membrane, and the hole opening method using the TEM device according to Non Patent Literature 1 and the hole opening method based on voltage application according to Non Patent Literature 2 were analyzed. However, by the hole opening method using the TEM device, there were the hole diameter variations on the order of 2 nm (3σ), and a hole position misalignment on the order of 5 nm (3σ), due to drifting. On the other hand, by the hole opening method based on voltage application, the hole diameter variations improved to 1 nm (3σ), and the system was also promising in terms of cost reduction and an increase in throughput; however, the hole opening position was indefinite in either the membrane having no structures or the membrane with the bow-tie or the electrode pair formed on the surface. In a blocking current system indicated in Non Patent Literature 2 (a system where the membrane has no structures other than a nanopore, and the blocking of an ion current through the nanopore by a molecule is measured), the hole position may not necessarily be accurately determined. However, in the optical measurement system using the near-field light due to a plasmon enhancement structure, or the tunnel current system using the electrode pair gap, position control for opening a hole at a predetermined position of the structure is required, not to mention a decrease in hole diameter and an increase in accuracy.

Solution to Problem

In order to solve the problems, a hole formation method according to the present invention includes repeating: a first step of, while an insulating film having a near-field light generating element placed thereon is being irradiated with light in an electrolytic solution, or after the film that has been irradiated with light is disposed in the electrolytic solution, applying a first voltage between a first electrode and a second electrode that are installed in the electrolytic solution across the film; and a second step of, after the first step, applying a second voltage between the first electrode and the second electrode, and detecting a value of a current that flows between the first electrode and the second electrode due to the application of the second voltage. The procedure of repeating the first step and the second step is stopped when the current value reaches or exceeds a pre-set threshold value.

A measurement device according to the present invention includes a light source that irradiates an insulating film having a near-field light generating element placed thereon with light; a mechanism for installing the film in a chamber; an introduction opening for introducing an electrolytic solution and a substance to be measured into the chamber having the film installed therein; a first electrode and a second electrode which are disposed across the film; a power supply for applying a voltage between the first electrode and the second electrode; an ammeter for detecting a current value obtained by applying a voltage; a control unit for controlling the light source and the power supply; and a storage unit storing a relationship between a size of a hole formed by applying a voltage to the film and a current value. The control unit, while the film is being irradiated with light or after the irradiation, repeats a control for applying a first voltage between the first electrode and the second electrode, and a second voltage between the first electrode and the second electrode after the application of the first voltage, and detecting a value of a current that flows between the first electrode and the second electrode due to the application of the second voltage. The control unit, when the current value reaches or exceeds a pre-set threshold value stored in the storage unit, stops the repetition of the control assuming that the hole has been formed in the film. Further, in order to measure a substance to be measured, such as a biomolecule, the measurement device may include a photodetector provided with a color identification mechanism for detecting light emitted, in response to the light from the light source, from the substance to be measured or a labeling luminous material attached to the substance to be measured as the substance passes through the hole. The storage unit may store a light detection value for each substance constituting the substance to be measured. In another configuration for measuring the substance to be measured, with respect to the value of a current that flows, due to the voltage application between the first electrode and the second electrode, as the substance to be measured passes through the formed hole, the storage unit may store a value for each substance constituting the substance to be measured.

Further, a hole formation method includes repeating: a first step of installing an insulating film having a pair of electrodes disposed thereon across a gap in an electrolytic solution, and, while a voltage is being applied to the electrode pair, or after the application of the voltage, applying a first voltage between a first electrode and a second electrode that are installed across the film; and a second step of, after the first step, applying a second voltage between the first electrode and the second electrode, and detecting a value of a current that flows between the first electrode and the second electrode second due to the application of the second voltage. The procedure of repeating the first step and the second step is stopped when the current value reaches or exceeds a pre-set threshold value.

Further, a measurement device according to the present invention includes a mechanism for installing in a chamber an insulating film having a pair of electrodes disposed thereon across a gap; an introduction opening for introducing an electrolytic solution and a substance to be measured into the chamber having the film installed therein; a first electrode and a second electrode which are disposed across the film; a first power supply for applying a, voltage between the first electrode and the second electrode; a second power supply for applying a voltage to the electrode pair; a first ammeter for detecting a value of a current obtained due to the voltage application by the first power supply; a control unit for controlling the first and second power supplies; and a storage unit storing a relationship between a size of a hole formed by applying a voltage to the film and a current value. The control unit repeats a control for, while a voltage is being applied to the electrode pair from the second power supply, or after the application, applying a first voltage between the first electrode and the second electrode, and a second voltage between the first electrode and the second electrode after the first voltage application, and for detecting a value of a current that flows between the first electrode and the second electrode due to the application of the second voltage, using the first ammeter. The control unit, when the current value reaches or exceeds a pre-set threshold value stored in the storage unit, stops the repetition of the control assuming that a hole has been formed in the film. Further, in order to measure the substance to be measured, the measurement device may include a second ammeter for detecting a value of a current that flows through the electrode pair as the substance to be measured passes through the formed hole. The storage unit, with respect to the current value, may store a value of each substance constituting the substance to be measured.

Advantageous Effects of Invention

Representative examples of the invention disclosed in the present description provide the following effect. In conventional nanopore device formation methods, when a hole is to be formed at a target position, variations in hole position or hole size on the order of several nanometers are unavoidable. However, the methods according to the present invention enable hole formation in accordance with a position suitable for measurement, and also enable the hole size to be controlled at angstrom level while the hole size is being highly accurately monitored. Accordingly, highly reproducible measurement can be performed using a nanopore for the optical measurement system or the tunnel current measurement system. The technique is simple, and cost reduction can also be expected.

BRIEF DESCRIPTION OF DRAWINGS

FIG. 19 describes an implementation example (conditions for hole opening and hole diameter measurement, and hole opening results).

DESCRIPTION OF EMBODIMENTS

An embodiment of the present invention will be described with reference to the drawings in which like reference signs denote elements with similar functions throughout, where redundant description of like elements is omitted whenever possible. In the following, the embodiment of the present invention will be described in detail with reference to the drawings. The device structures and materials described in the implementation examples are examples for embodying the concept of the present invention, and are not intended to strictly specify relevant materials, size, and the like.

Implementation Example 1

The above-described problems can be solved by a method described in the following implementation example.

A first implementation example will be described in which a plasmon enhancement structure is provided on a membrane, the plasmon enhancement structure being a bow-tie structure by way of example, wherein a hole is accurately formed in the gap of the bow-tie structure.

Figure 1:
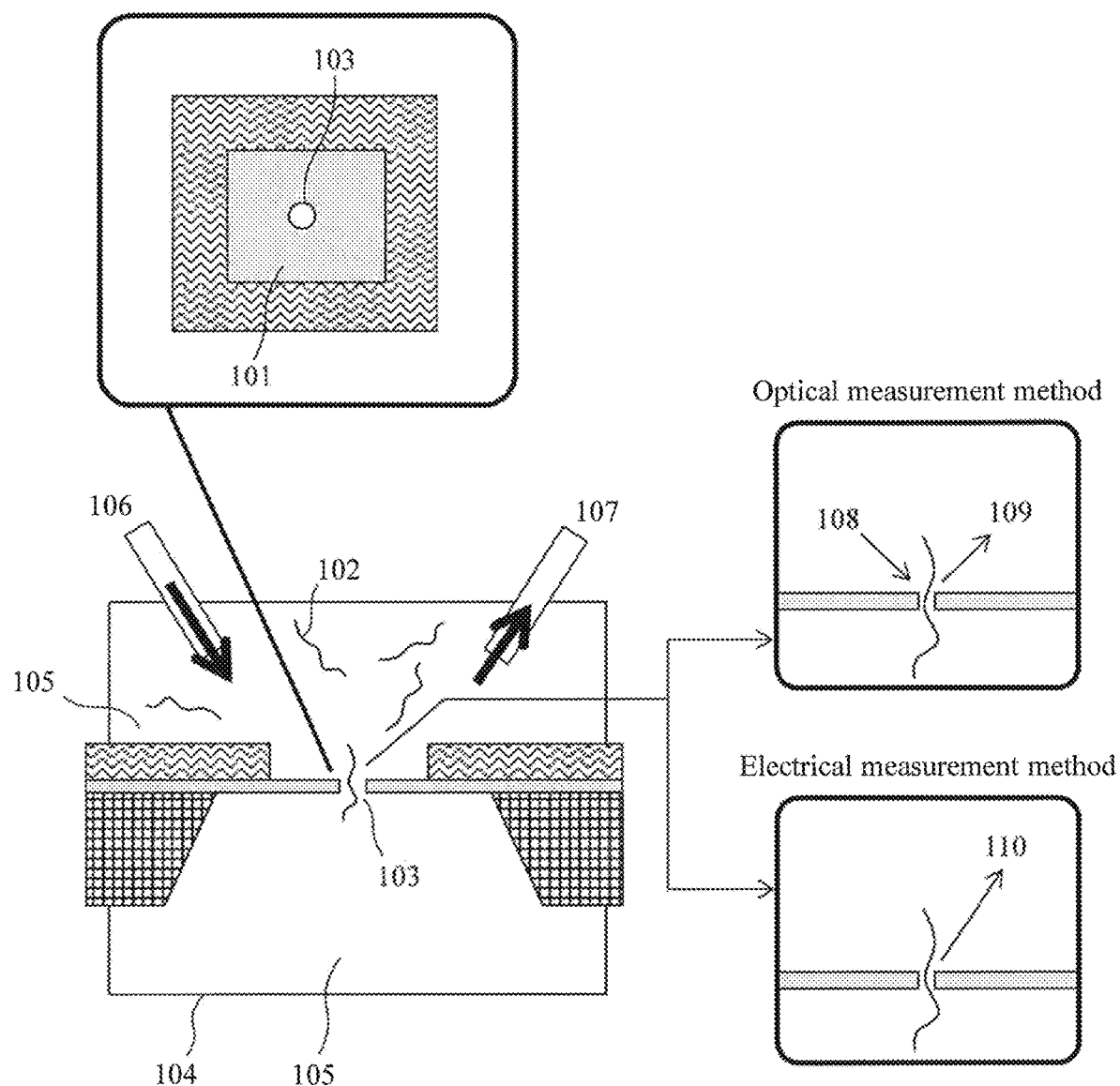
FIG. 1 illustrates the principle of nanopore measurement.
Figure 2:
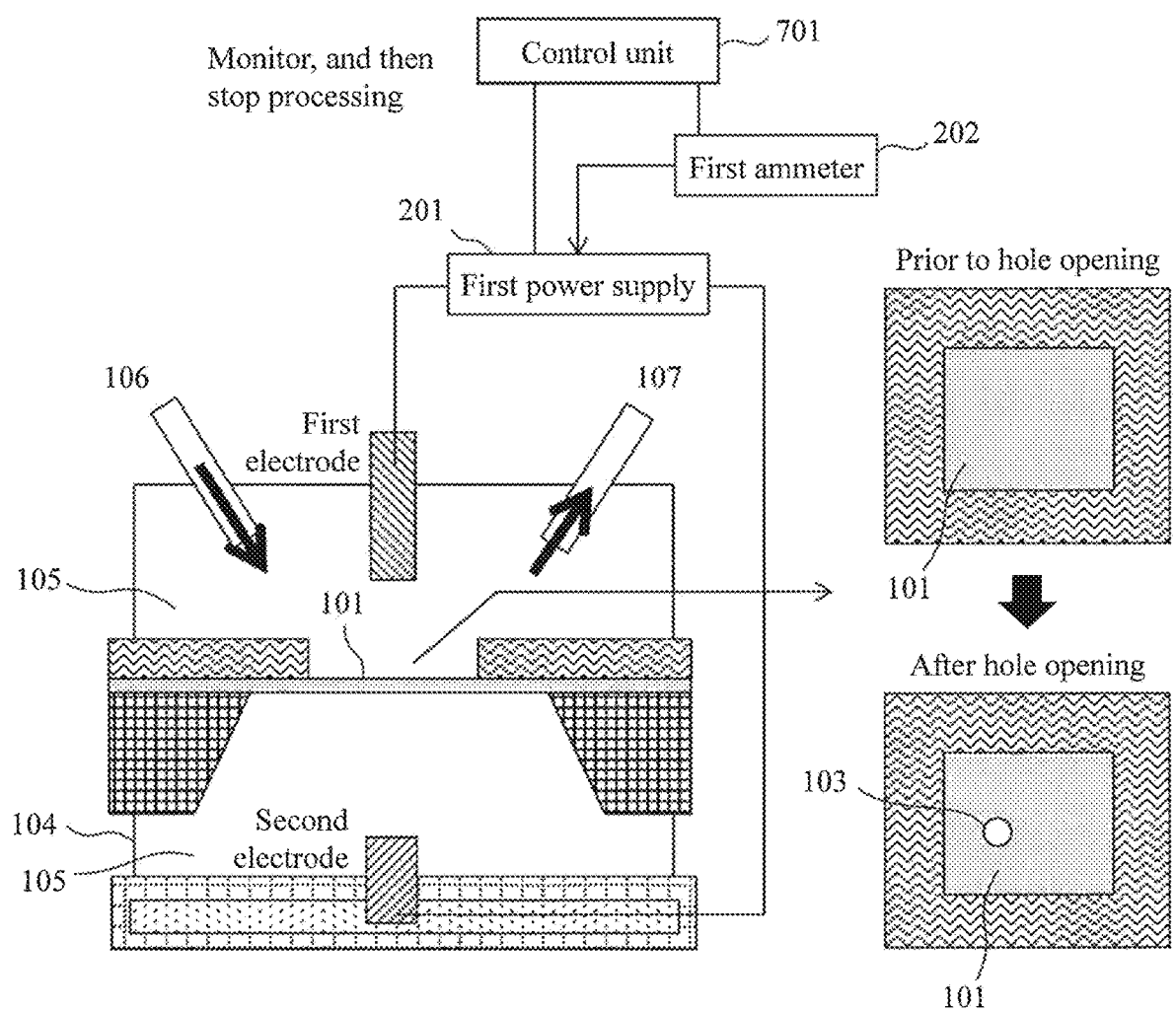
FIG. 2 describes a problem of a hole opening method.
Figure 3:
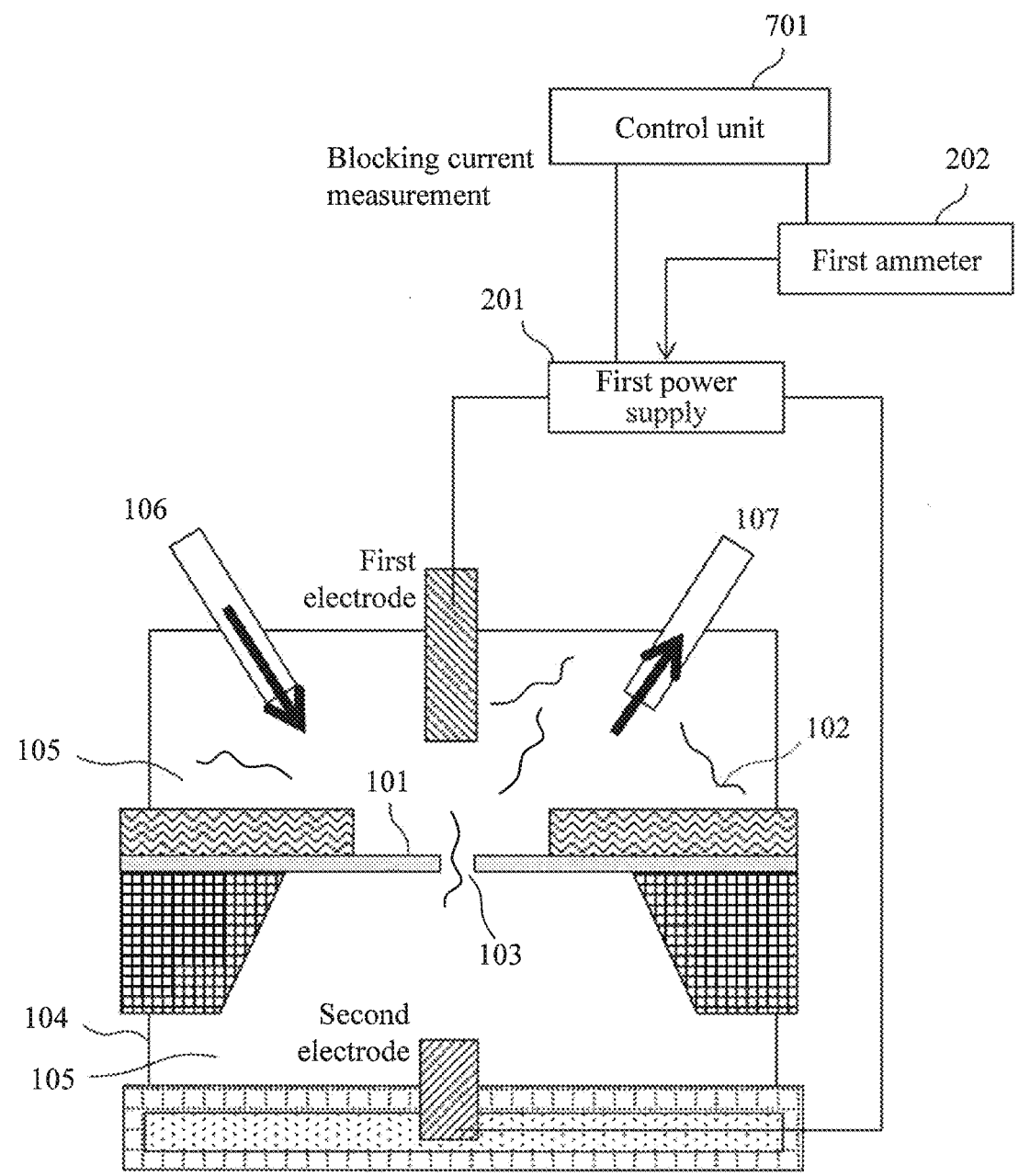
FIG. 3 describes a DNA analysis method.
Figure 4A:
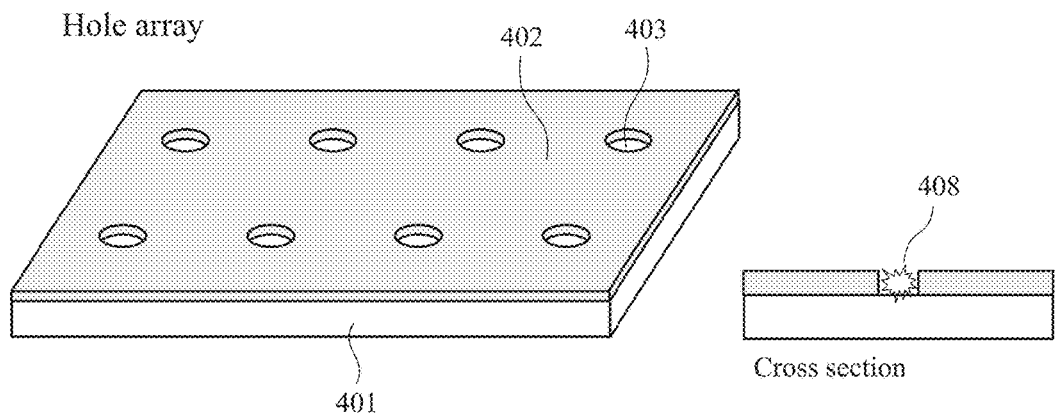
FIGS. 4A-4C illustrate examples of plasmon enhancement structures and near-field light generated positions.
Figure 4B:
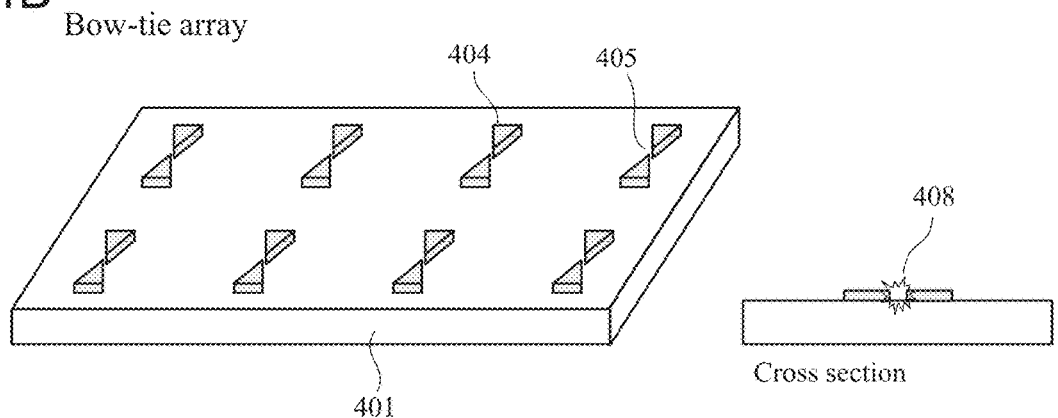
Figure 4C:
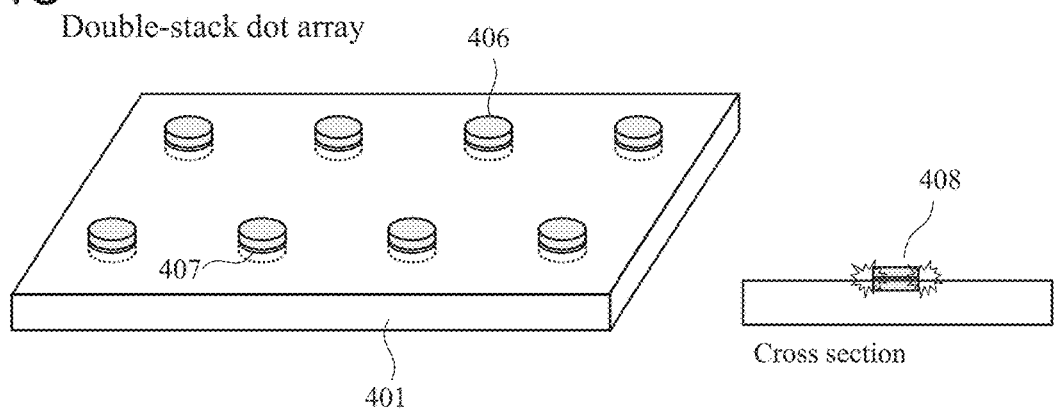
Figure 5A:
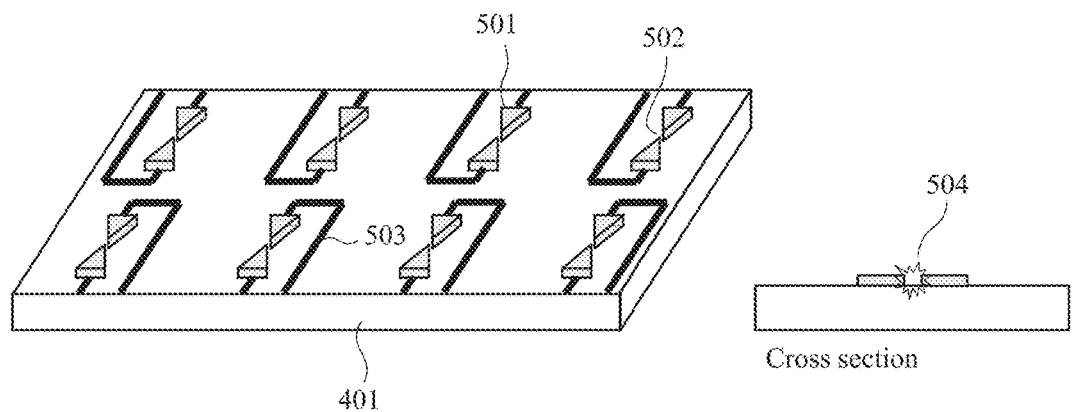
FIGS. 5A and 5B illustrate pairs of tunnel current measuring electrodes and an example of wiring therefor.
Figure 5B:
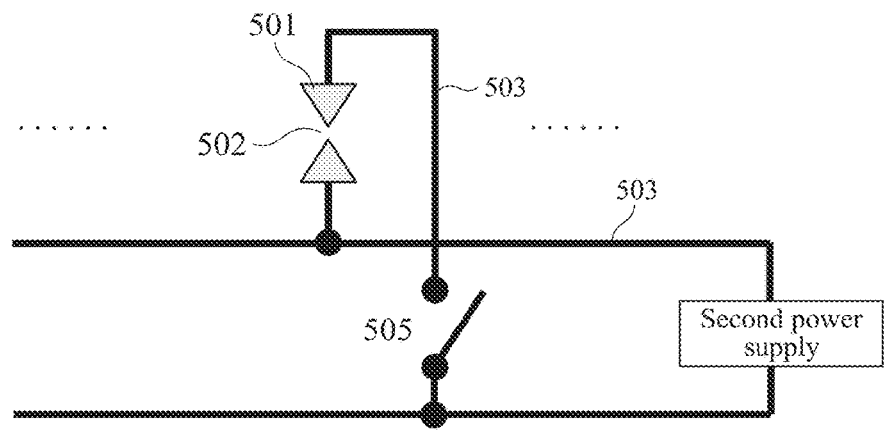
Figure 6:
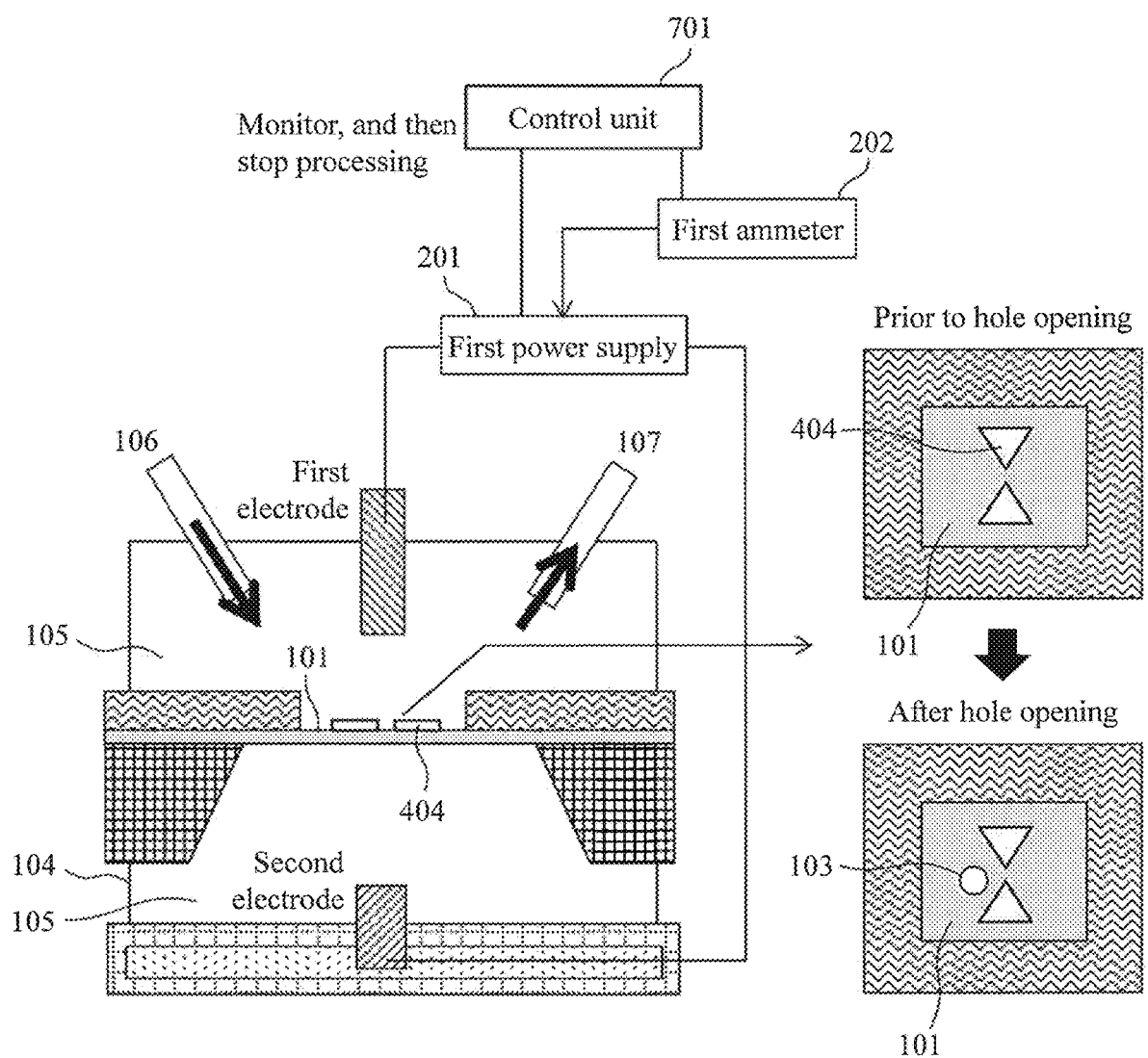
FIG. 6 describes a problem of a hole opening method.
Figure 7:
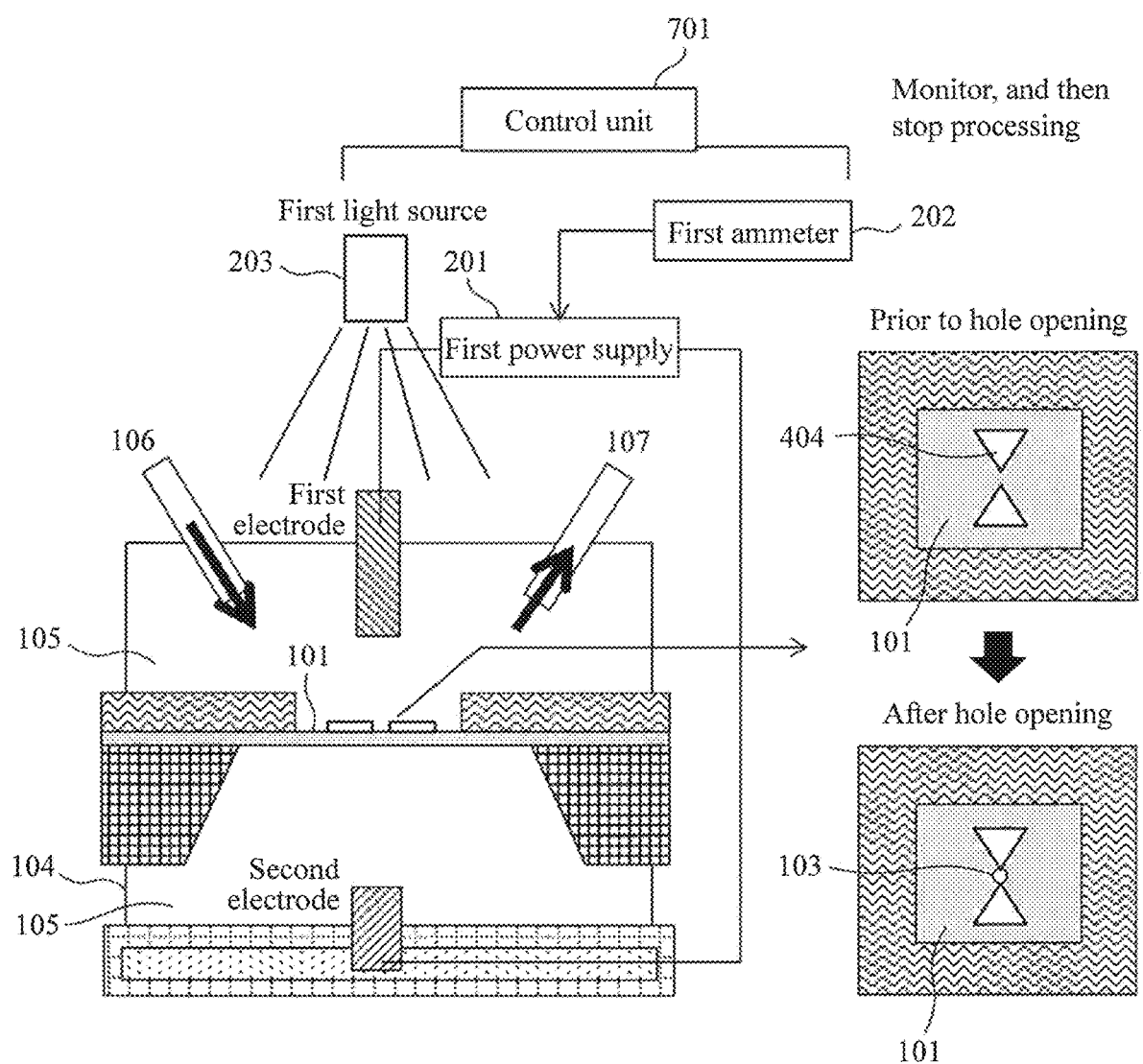
FIG. 7 describes an example of implementation of hole opening by a plasmon enhancement structure according to the present invention.

FIG. 7 illustrates an overall device structure. A chamber 104 is provided with an aqueous solution inlet port 106 for introducing an aqueous solution 105 containing an electrolytic solution and the like, and an outlet port 107. The chamber 104 includes a mechanism for installing an insulating film 101 between a first electrode and a second electrode. Via the aqueous solution inlet port 106, the electrolytic solution, a substance to be measured and the like can be introduced into the chamber 104. On the insulating film 101, a near-field light generating element 404 that generates near-field light when irradiated with light is placed, as illustrated in FIG. 4. The device is provided with a light source 203 that irradiates the near-field light generating element 404 with light. The device is further provided with a first power supply 201 for applying a voltage between the first electrode and the second electrode; a first ammeter 202 for sensing a current that flows between the first electrode and the second electrode due to the voltage application; and a control unit 701 for controlling the above units. The control unit 701 includes a processor, a memory and the like necessary for controlling the power supply, the light source, and the like.

A specific example will be described.

In the chamber, there was loaded a chip with the bow-tie structure 404 formed on a $Si_3N_4$ membrane 101 with a thickness of 10 nm and having no hole, the bow-tie structure having two conductor dots of a size of approximately 40 nm disposed proximate to each other. Both sides of the chamber isolated by the membrane were filled with the KCl aqueous solution 105, and the first electrode and the second electrode were respectively immersed in the KCl aqueous solution in either side of the chamber. In order to form a hole in the membrane, in a dark environment created by placing a shielding box around the chamber 104 to block light, initially a voltage of 4 V was applied between the first electrode and the second electrode for two minutes, using the first power supply. Then, in order to measure the hole diameter, a voltage of 4 V was applied between the electrodes for 30 seconds, and a current value was accurately measured. This procedure (first procedure) was repeated, whereby in the sixth repetition, the current value increased to 800 pA when the voltage of 4 V for measuring the hole diameter was applied. Accordingly, by comparing with data previously obtained by determining the relationship between hole diameter and current value, it was confirmed that a hole was opened in the membrane and a hole diameter of 2 nm was reached.

Figure 12:
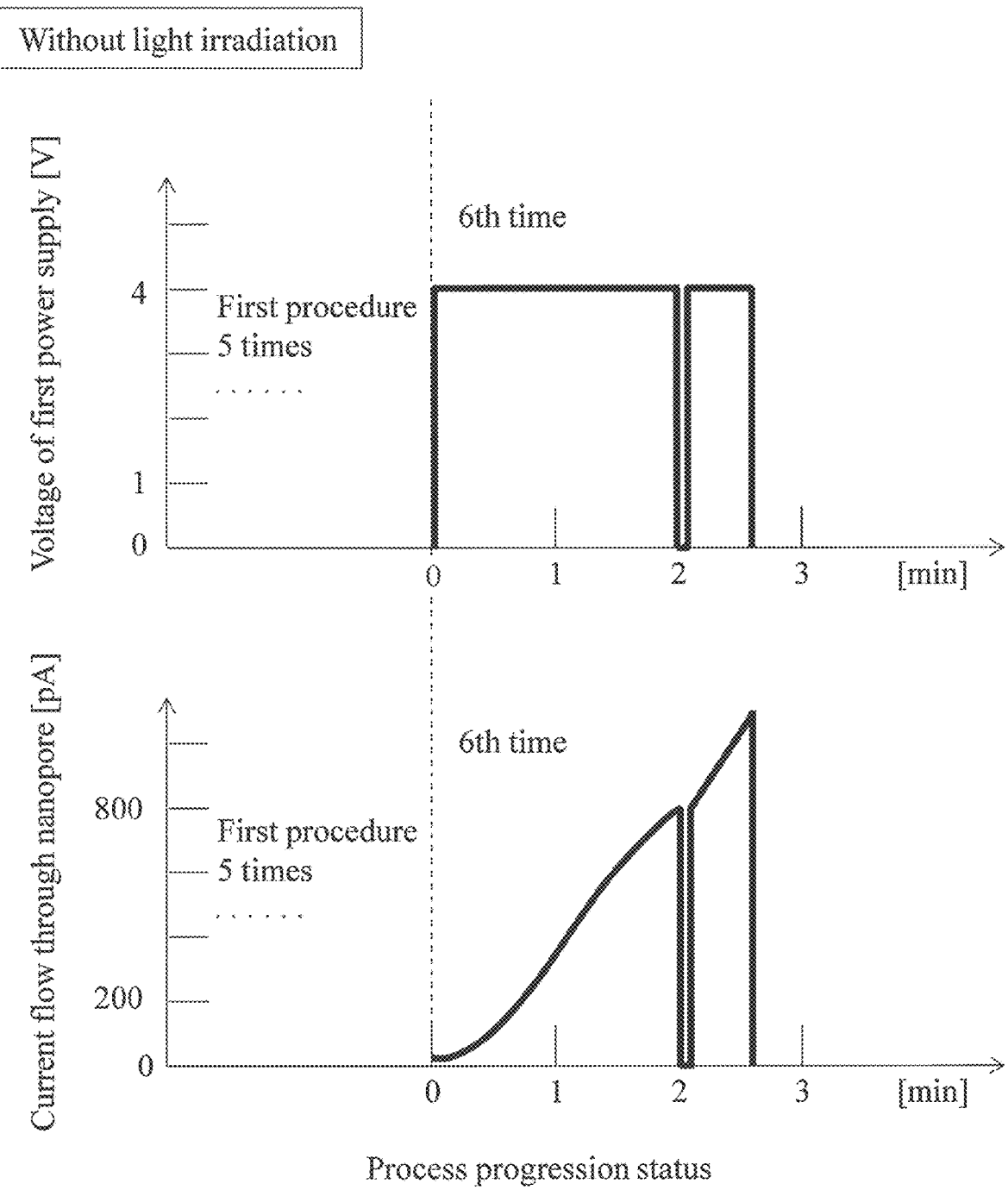
FIG. 12 illustrates data for describing an example of implementation of hole opening according to the present invention.

However, the current value that had been 800 pA (corresponding to the hole diameter of 2 nm) immediately after the application of the measuring voltage of 4 V increased to 1060 pA (corresponding to a hole diameter of 2.3 nm) 30 seconds after the start of application of the measuring voltage (FIG. 12). It is desirable that in the period in which a voltage for measuring the hole diameter is being applied, the hole does not expand. While the hole of 2 nm had been formed in the initial two minutes by voltage application in the solution, it is believed that the hole diameter increased in the additional 30 seconds because the voltage of 4 V applied for the subsequent hole diameter measurement was too high. In addition, the hole was formed at a position that had no relationship with the bow-tie structure formed on the membrane.

Figure 13:
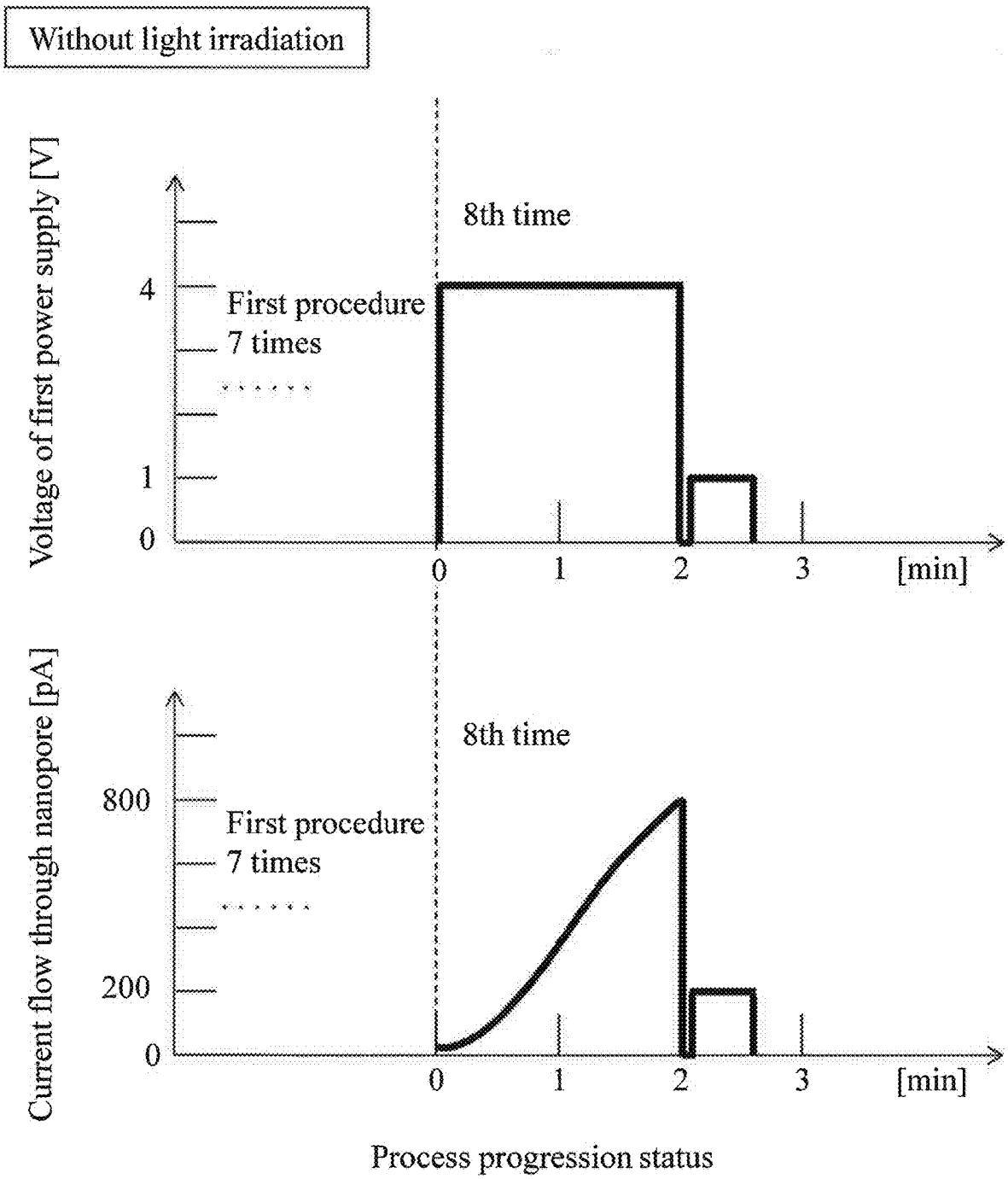
FIG. 13 illustrates data for describing an example of implementation of hole opening according to the present invention.

Thus, in the dark environment blocking light with the shielding box, a voltage of 4 V was applied between the first electrode and the second electrode for two minutes using the first power supply, and then, this time, the voltage for measuring the hole diameter was lowered. Specifically, a voltage of 1 V was applied for 30 seconds between the electrodes, and the current value was accurately measured. When this procedure (first procedure) was repeated, in the 8th repetition, the current value when the hole opening voltage of 4 V was applied increased to 800 pA (corresponding to a hole diameter of 2 nm). Immediately thereafter, a voltage of 1 V for hole diameter measurement was applied for 30 seconds. From the start of the hole diameter measurement to the end of measurement 30 seconds later, the current that flowed through the hole remained at 200 pA (corresponding to the hole diameter of 2.0 nm) and was substantially unchanged, due to the effect of lowering the voltage (FIG. 13). It is believed that the hole was formed in the initial two minutes, and that the hole diameter of 2.0 nm was successfully accurately measured without an increase in the hole diameter because the current flow through the hole was measured using a lower voltage in the subsequent 30 seconds. However, the hole kept being formed at random positions having no relationship with the position of the bow-tie structure on the membrane, no matter how many times the procedure was tried.

While up to this point, the position of hole formation was indefinite, the following guidelines with regard to the applied voltage and the time of application were gained. In the case of the $Si_3N_4$ membrane used for hole formation and having a thickness of 10 nm without a hole, when the application of a voltage of 4 V was continued, a hole was formed and the hole diameter increased little by little. On the other hand, when a voltage of 1 V was applied, an ion current flowed through the hole, and, while the hole diameter was able to be estimated from the current value, the hole diameter did not increase. In this example, the formation of a hole of approximately 2 nm was completed by repeating the voltage application six to eight times. However, if the applied voltage is increased above 4 V with the same membrane thickness, or in the case of a thinner membrane, for example, the amount of expansion of the hole will become greater per two minutes of voltage application, whereby the desired hole diameter will be reached in a smaller number of times of voltage application. The hole will also be opened in a smaller number of times of voltage application if the material is changed to one with smaller insulating resistance. As the required number of times becomes smaller, the voltage application may fail to be stopped at a target hole diameter, and may pass the target hole diameter. In such a case, the two-minute intervals of the hole opening voltage application may be changed to one-minute intervals, for example, so that the gradual increase in hole diameter can be confirmed by measuring the hole diameter at the intervals using a voltage of 1 V. In this way, more accurate positioning with respect to the target hole diameter can be achieved. In the present example, the time for hole diameter measurement was fixed at 30 seconds. However, because the hole would not expand during the hole diameter measurement if the voltage is decreased to 1 V, the time of 30 seconds for the hole diameter measurement may be changed as needed. In the present implementation example, the ion current being measured included noise, so that the hole diameter error was large at 10% or more during several seconds of measurement. However, by measuring the current for 30 seconds and averaging the noise, it became possible to estimate the hole diameter with an error of less than 10%.

Figure 14:
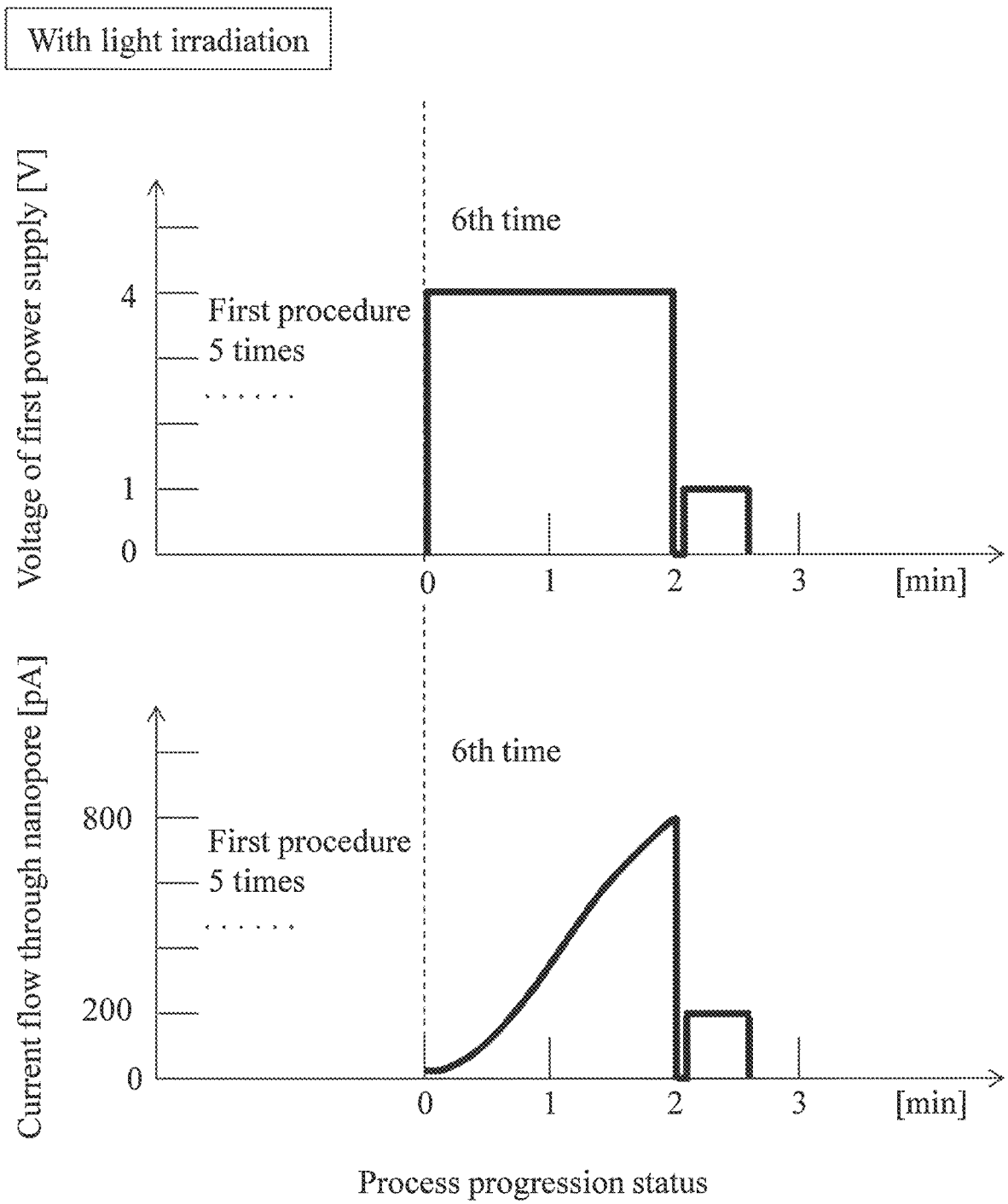
FIG. 14 illustrates data for describing an example of implementation of hole opening according to the present invention.

Accordingly, the first light source was installed in the shielding box and turned ON, and the plasmon enhancement structure (bow-tie structure 404) formed on the membrane 101 was irradiated with light so as to cause near-field light to be generated at the bow-tie gap position. In the present implementation example, the light source was a laser with a wavelength of 785 nm and an output of 50 mW. In this situation, the first electrode and the second electrode were respectively immersed in the KCl aqueous solution 105 in either side of the chamber 104 isolated by the membrane (FIG. 7), and then a voltage of 4 V was applied between the electrodes for two minutes using the first power supply, in an attempt to open a hole. Thereafter, in order to estimate the hole diameter, the first light source was turned off, a voltage of 1 V was applied between the electrodes for 30 seconds, and the current value was accurately measured. This was repeated six times, and when the hole opening voltage of 4 V was applied, the current value increased to 800 pA (corresponding to the hole diameter of 2 nm), indicating the formation of a hole. When the voltage of 1 V for hole diameter measurement was applied immediately thereafter, the current that flowed through the hole was 200 pA (corresponding to the hole diameter of 2.0 nm) and the current remained unchanged for 30 seconds and was stabilized (FIG. 14). Accordingly, as in the case of implementation under the dark environment in which light was blocked by the shielding box, it was possible to accurately form a hole and to estimate the hole diameter without an increase during the measurement.

Figure 15:
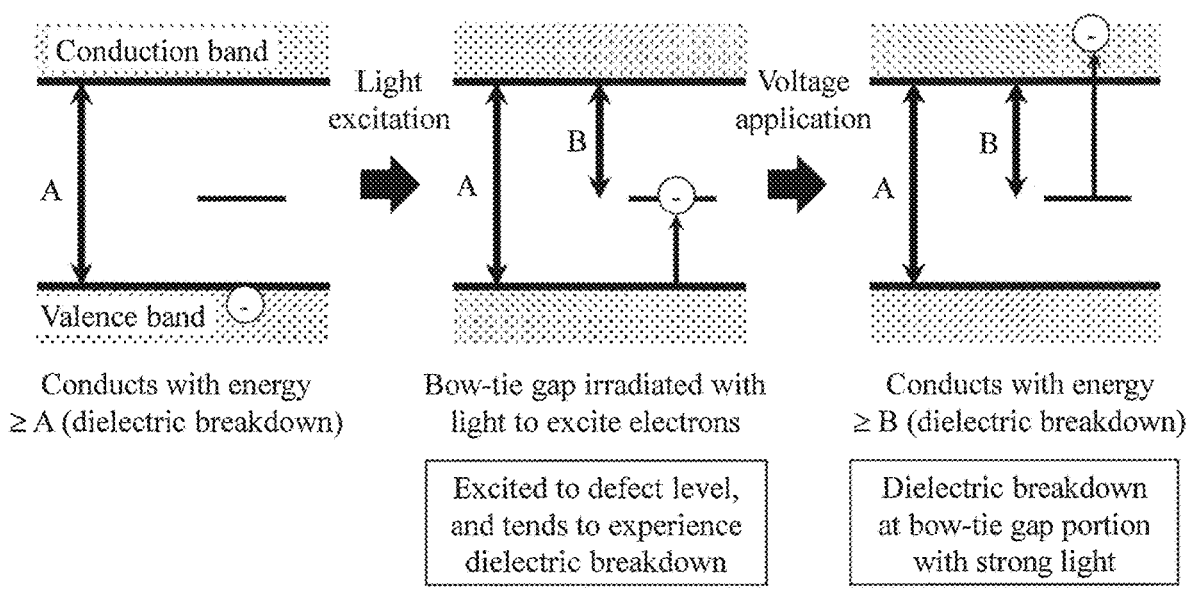
FIG. 15 illustrates a hole opening mechanism according to the present invention.

When the vicinity of the bow-tie structure was carefully observed in search of the position where the hole was formed, it was learned that the 2.0 nm hole had been formed at the bow-tie gap position. This is believed due to the fact that the irradiating light was extremely enhanced by the bow-tie at the gap position, causing a high-density excitation of the electron state of the membrane material in the vicinity of the gap, which in turn made it easier for dielectric breakdown to occur, resulting in the formation, due to the voltage application between the first electrode and the second electrode, of the hole at the gap position where the near-field light was the strongest (FIG. 15).

When estimating the hole diameter, the current that flows through the hole can be measured by applying the voltage of 1 V between the first electrode and the second electrode using the first power supply, without turning off the light source, i.e., with the optical irradiation continued. However, the light source may preferably be turned off at the time of application of the hole diameter measurement voltage in light of the possible loss of accuracy of values due to the influence of charge-up caused by light, for example.

While in the forgoing the hole formation was performed by voltage application while light irradiation was being performed, the near-field light generating element on the membrane may be irradiated with light in advance so that a predetermined position can be degraded by light enhancement in the vicinity of the near-field light generating element. Then, in this state, the membrane may be installed in the electrolytic solution in the chamber, followed by voltage application to perform hole formation.

Figure 16:
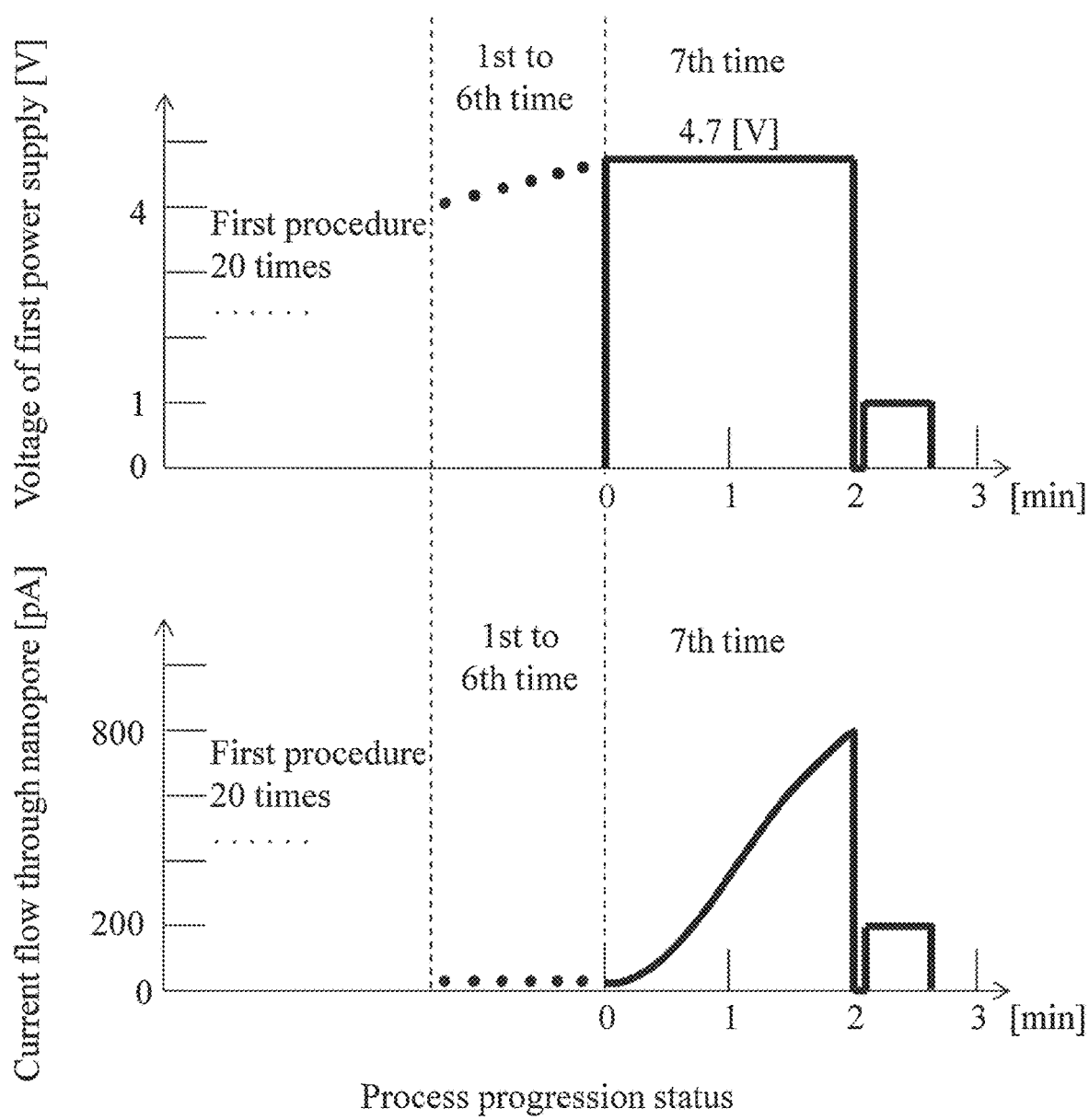
FIG. 16 illustrates data for describing an example of implementation of hole opening according to the present invention.

Meanwhile, similar hole opening was implemented, on a trial basis, with respect to a chip in which the bow-tie structure had been formed on a $Si_3N_4$ membrane having a thickness of 15 nm and having no hole. When exactly the same conditions as in the case of the membrane with a thickness of 10 nm were applied, including the strength of irradiating light from the first light source and the voltage applied between the first electrode and the second electrode, it was not possible to form a hole even after the procedure of the 4-volt, 2-minute hole opening and the 1-V, 30-seconds hole diameter measurement was repeated up to 20 times. Accordingly, a control was implemented such that, for each repetition of the series of procedure (first procedure) including the voltage application for hole opening and the voltage application for hole diameter measurement, the hole opening voltage (first voltage) was incremented by +0.1 V from 4 V. Then, the current value showed an increase during the 7th repetition when the hole opening voltage became 4.7 V, indicating the formation of a hole (FIG. 16). Thus, while there are factors such as membrane thickness variations and variations in the insulating resistance of the membrane material at the position to be penetrated, when it is difficult to form a hole, one good method is to increase the hole opening voltage from a lower value little by little. In this way, the variations in the ease of hole formation can be absorbed, whereby a membrane chip provided with a desired hole can be manufactured with high yield.

Meanwhile, in order to examine the influence of the strength and wavelength of laser light, two experiments were conducted on a trial basis with respect to a chip in which the bow-tie structure was formed on a $Si_3N_4$ membrane having a thickness of 10 nm and having no hole. In one experiment, the laser light intensity was increased by a factor of 10, while the hole opening voltage was lowered to 2 V; in the other, the wavelength of laser light was changed to a shorter wavelength of 638 nm, and the hole opening voltage was lowered to 2 V. It was learned that, despite the lowering of voltage to 2 V, a hole was able to be formed at the bow-tie gap position. This is probably due to an increase in excitation density at the bow-tie gap position, or to excitation up to a higher energy level. It was also learned that, even if the hole diameter measurement voltage applied in the 30 seconds after the two minutes of hole opening voltage application at 2 V was set to be the same 2 V as the hole opening voltage for simplification, the hole diameter would not expand for the 30 seconds if the laser light is turned off during the hole diameter measurement. Accordingly, it was learned that, as a procedure for repeating the hole opening and hole diameter measurement, besides the method of lowering the voltage at the time of hole diameter measurement, the voltage for hole opening and the voltage for hole diameter measurement may be simply made the same, and the light irradiation at the time of hole opening may be performed and simply turned off at the time of hole diameter measurement. In this way, too, desired hole opening conditions such that the hole would not expand at the time of hole diameter measurement can be set.

The evaluation results so far are organized and shown in FIG. 19. At the time of hole opening, the hole position is indefinite under conditions A and B for light irradiation OFF. On the other hand, under conditions C, D, and E for light irradiation ON, a hole with a desired diameter was able to be formed at a desired position either by the method where the voltage was lowered at the time of hole diameter measurement (C), or by the method where the output (D) or energy (E) of light was increased at the time of hole opening, and where only the light is turned OFF without lowering the voltage at the time of hole diameter measurement.

Implementation Example 2

A second implementation example will be described with reference to FIG. 8 in which a pair of tunnel current measuring electrodes was provided on a membrane, and a hole was formed in a gap between the pair of tunnel current measuring electrodes.

Figure 8:
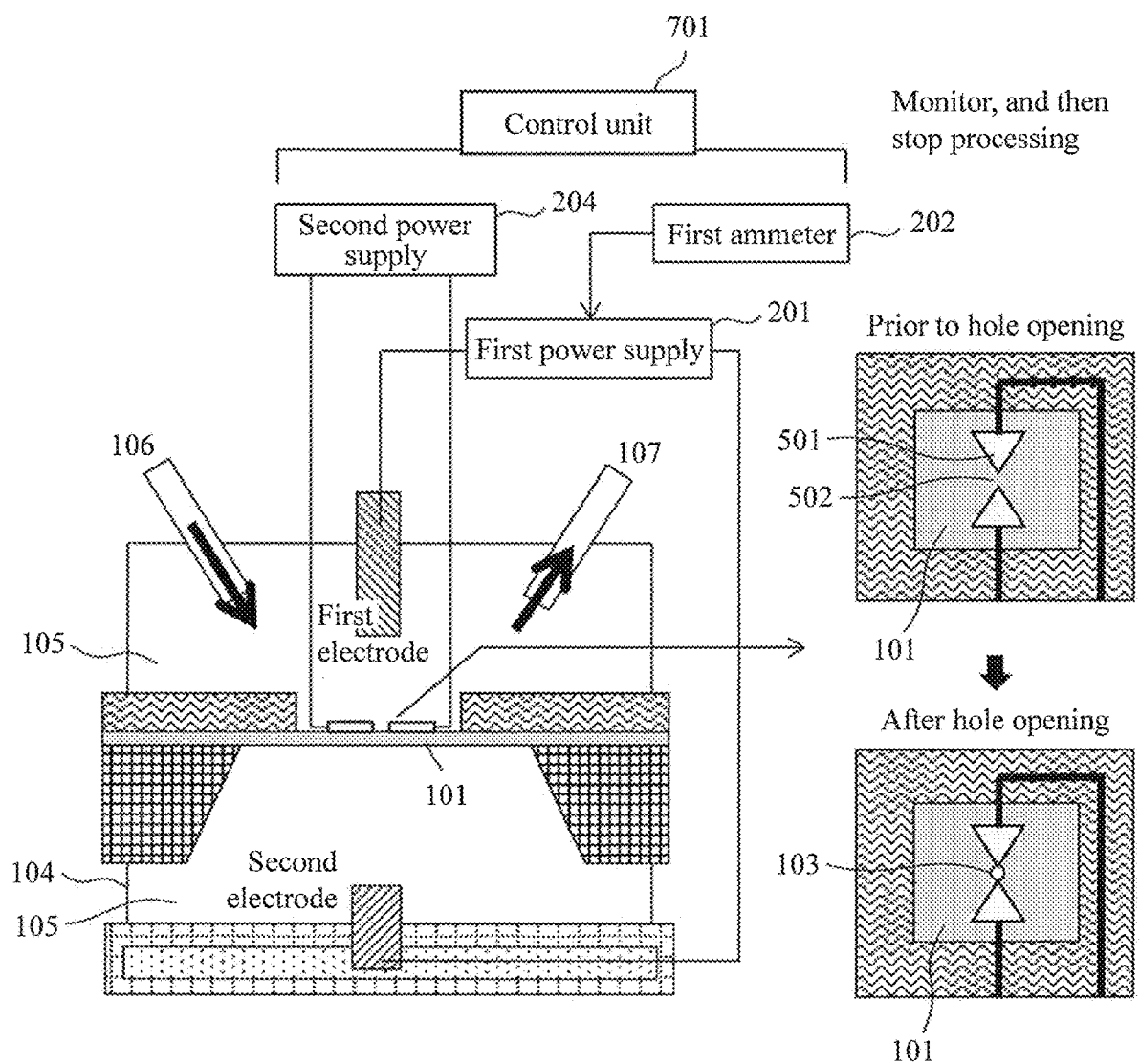
FIG. 8 describes an example of implementation of hole opening using a pair of tunnel current measuring electrodes according to the present invention.

FIG. 8 illustrates the device as a whole, of which description of portions corresponding to FIG. 7 is omitted. In FIG. 8, the insulating film 101 is provided with an electrode pair

501, to which a voltage is applied from a second power supply 204. A hole is formed in the gap of the electrode pair 501 by implementing the voltage application method such as described in Implementation Example 1, while the voltage is being applied to the electrode pair 501, or after the voltage application thereto. In the following, a specific example will be described.

In the chamber, there was loaded a chip in which the electrode pair 501 was formed on a $Si_3N_4$ membrane having a thickness of 10 nm and having no hole, with the gap 502 of 3 nm disposed at the position where the tip ends of the electrode pair were opposed to each other. The second power supply for applying a voltage to the electrode pair 501 was also connected. Both sides of the chamber isolated by the membrane were filled with the KCl aqueous solution, the first electrode and the second electrode were respectively immersed in the KCl aqueous solution in either side of the chamber, and the first power supply was connected to the electrodes. While there may be no influence of light as the present device was different from the optically excited device of Implementation Example 1, the experiment was conducted under the same light-shielded dark environment in a shielding box as used in Implementation Example 1 so as to form a hole in the membrane in the identical experiment environment for comparison.

First, in a state where no voltage (second power supply) was being applied to the pair of tunnel current measuring electrodes, a voltage of 4 V was applied between the first electrode and the second electrode for two minutes, using the first power supply. Then, in order to measure the hole diameter, a voltage of 1 V was applied between the electrodes for 30 seconds, and the current value was accurately measured. By repeating this, a 2 nm hole was formed in the membrane as in the case of the membrane with the bow-tie according to Implementation Example 1. However, the hole formation position was an irrelevant position spaced apart from the pair of tunnel current measuring electrodes.

Accordingly, next, a voltage of 2 V was applied to the pair of tunnel current measuring electrodes 501 using the second power supply 204, and a voltage was applied to the gap 502 of 3 nm at the tip-end portions of the electrode pair on the membrane having no hole. Because the gap was filled with the KCl aqueous solution, a current flowed through the gap 502 of the electrode pair. In this situation, the first electrode and the second electrode were respectively immersed in the KCl aqueous solution in either side of the chamber isolated by the membrane, and hole opening was attempted by applying a voltage of 4 V between the electrodes for two minutes, using the first power supply. Thereafter, in order to estimate the hole diameter, the voltage applied to the gap of the tip-end portions of the pair of tunnel current measuring electrodes 501 was turned off, a voltage of 1 V was applied between the first electrode and the second electrode for 30 seconds, using the first power supply, and the current value was accurately measured. As a result, the current value was 250 pA and remained substantially unchanged for 30 seconds, making it possible to confirm that a hole was formed. When the vicinity of the gap at the electrode tip-end portions of the pair of tunnel current measuring electrodes was carefully observed in search of the position where the hole had been formed, it was confirmed that a hole which was nearly elliptical with the major axis of 2.2 nm and the minor axis of 2.0 nm had been formed at the gap position of the electrode tip-end portions.

Compared with the case of the hole formed in the bow-tie gap, the shape of the hole was slightly extended between the tip-end portions of the pair of tunnel current measuring electrodes in the direction of the electrode tip ends. It is believed that the hole was formed at the gap position between the electrode tip-end portions because a current was induced in the gap of the electrode tip-end portions by the voltage applied from the second power supply, and then the electron excitation state or charge state of the membrane material was changed, making it easier for dielectric breakdown to occur.

Implementation Example 3

As indicated by Implementation Example 1 and Implementation Example 2, it became possible to determine the hole opening position by exciting a specific position on the membrane using a functional structure that enables light enhancement, localized current excitation and the like. In the following, a third implementation example will be described in which, of the example in which the bow-tie was provided on the membrane as the plasmon enhancement structure and the example in which a pair of tunnel current measuring electrodes was provided on the membrane, the example in which the bow-tie was provided on the membrane as the plasmon enhancement structure was used, where the relationship among hole opening voltage, the number of times of voltage application, and the time it took for hole completion (throughput) was investigated.

Figure 17:
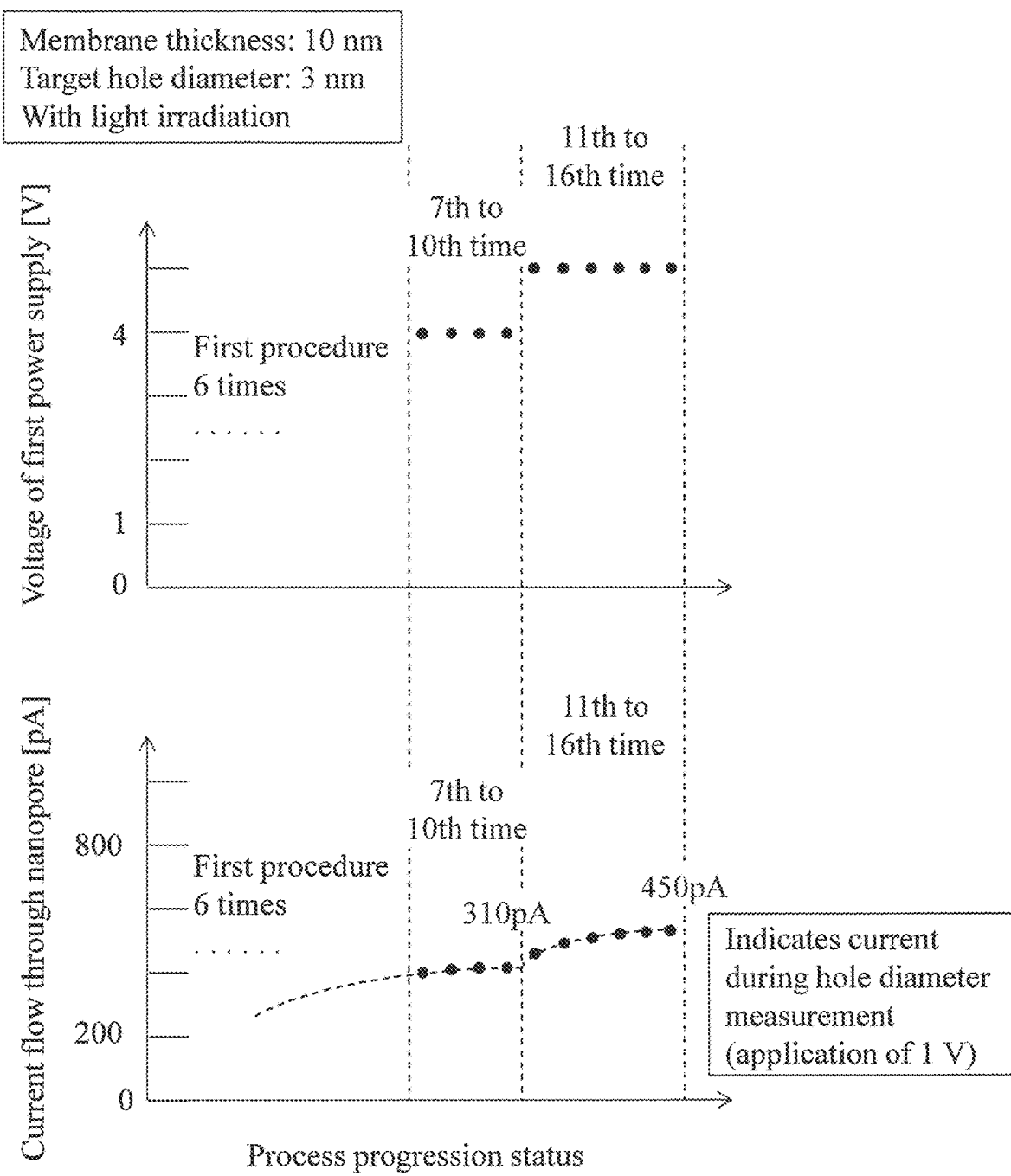
FIG. 17 illustrates data for describing an example of implementation of hole opening according to the present invention.

In the chamber, there was load a chip in which a bow-tie structure comprising two conductor dots with a size of approximately 40 nm disposed proximate to each other was formed on a $Si_3N_4$ membrane having a thickness of 10 nm and having no hole, both sides of the chamber isolated by the membrane were filled with the KCl aqueous solution, and the first electrode and the second electrode were immersed in the KCl aqueous solution in either side of the chamber. In the present Implementation Example 3, the aim was to open a hole of 3 nm. In order to form the hole in the membrane, the first light source installed in the shielding box was turned ON, and the plasmon enhancement structure (bow-tie structure) formed on the membrane was irradiated with light so as to generate near-field light at the bow-tie gap position. In this state, a voltage of 4 V was applied between the first electrode and the second electrode for two minutes, using the first power supply. Then, in order to measure the hole diameter, a voltage of 1 V was applied between the electrodes for 30 seconds, and the current value was accurately measured. This procedure (first procedure) was repeated, and the plan was to stop the process when the current reached 450 pA (corresponding to a hole diameter of 3 nm). However, while the procedure was repeated in an attempt to achieve the diameter of 3 nm, it was learned that, even if the first procedure was repeated ten times, the increase in current value tended to be saturated at around 310 pA in the 8th, 9th, and 10th repetitions, as illustrated in FIG. 17. This was interpreted, according to a calculation of the hole diameter based on the current value, to indicate that the enlargement of the hole becomes saturated at around the hole diameter of 2.5 nm.

Accordingly, the first procedure was performed ten times and then switched, at the point in time when the current at the time of application of the 1 V for hole diameter measurement became 310 pA, to a process (second procedure) with an increased applied voltage. From the 11th voltage application, the applied voltage setting for hole opening was increased from 4 V to 5 V. Thereafter, the procedure (second procedure) for measuring the hole diameter with 1 V was additionally implemented six times (for a total of 16 times). As a result, as illustrated in FIG. 17 from the 11th to 16th repetitions, an increasing tendency from 310 pA was observed, and it was decided that the current of 450 pA (hole diameter of 3 nm) was reached at the time of the 16th application of 1 V for hole diameter measurement.

Another chip with a membrane having a thickness of 10 nm with no hole and having the bow-tie was prepared on a trial basis, and the first procedure was repeated with a high applied voltage of 5 V for hole opening from the first time. As a result, the current at the time of application of the voltage of 1 V for hole diameter measurement reached 450 pA (corresponding to a hole diameter of 3 nm) by the 8th repetition.

Thus, when the hole opening was performed by repeating the first procedure with a constant applied voltage from the first power supply, the enlargement of the hole tended to saturate as the number of times of repetition was increased. Therefore, when it is desired to additionally enlarge the hole or to form a large hole from the beginning, it is hard to reach the desired hole diameter by simply increasing the number of repetitions alone. When the hole diameter is to be additionally enlarged or a slightly larger hole is to be formed, the time it takes for hole completion can be decreased by implementing the procedure with a higher hole opening voltage, as it was learned. However, if the voltage is too high from the beginning, the desired hole diameter could be exceeded by implementing the first procedure for just a small number of times. Because the hole once expanded too much cannot be made smaller again, it is preferable to employ a method whereby initially, a smaller hole is aimed at, and then the hole is slightly enlarged during the course by switching the voltage, before the hole is completed.

While as illustrated in FIG. 17, the hole of 3 nm diameter was eventually reached by increasing the voltage from 4 V to 5 V, there still remained the tendency, even at 5 V, for gradual saturation. Accordingly, as the diameter becomes closer to 3 nm, the amount of enlargement in the hole diameter achieved at one time was decreased, resulting in a greater number of times and therefore a decrease in efficiency. Based on a prior understanding of such saturation characteristics, a control method may be effectively implemented so as to gradually extend the processing time as the processing is repeated, whereby the number of times toward the latter half of the processing can be decreased, and the desired hole diameter can be reached efficiently.

Implementation Example 4

A fourth implementation example will be described in which, after the hole opening was completed, the hole diameter as measured with increased accuracy by applying the hole diameter measurement voltage.

Figure 18A:
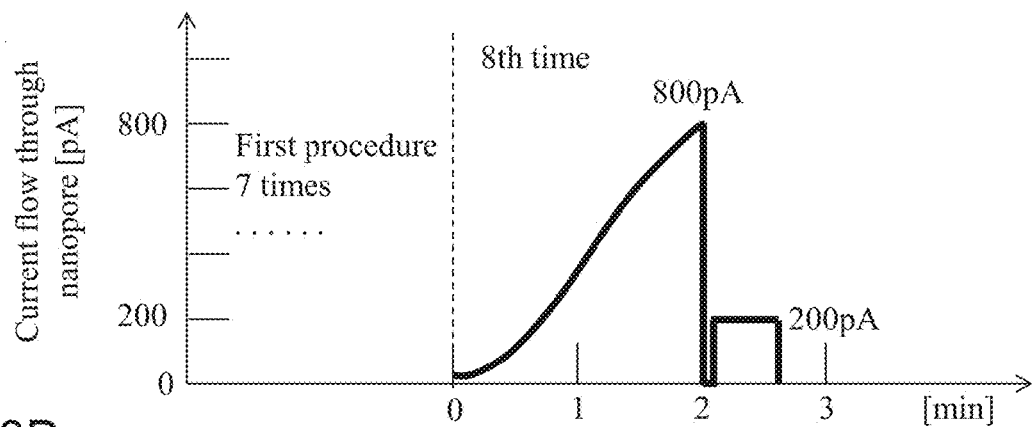
FIGS. 18A-18C illustrate data for describing an example of implementation of hole opening according to the present invention.
Figure 18B:
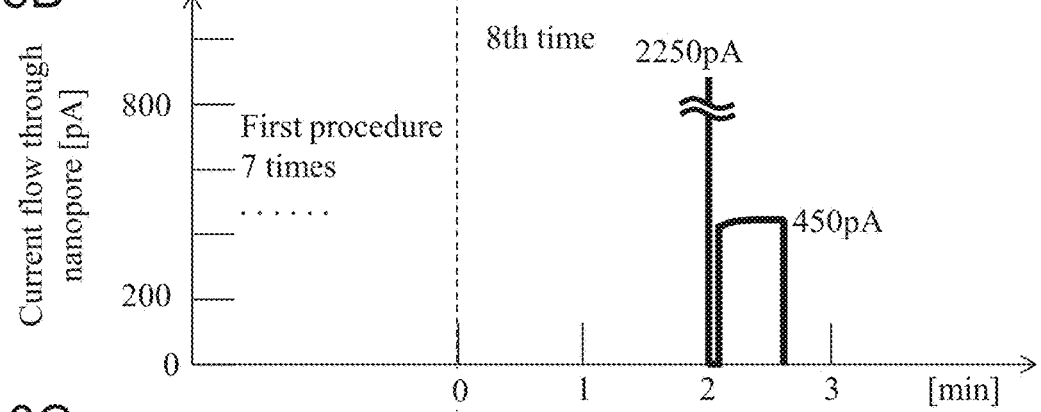
Figure 18C:
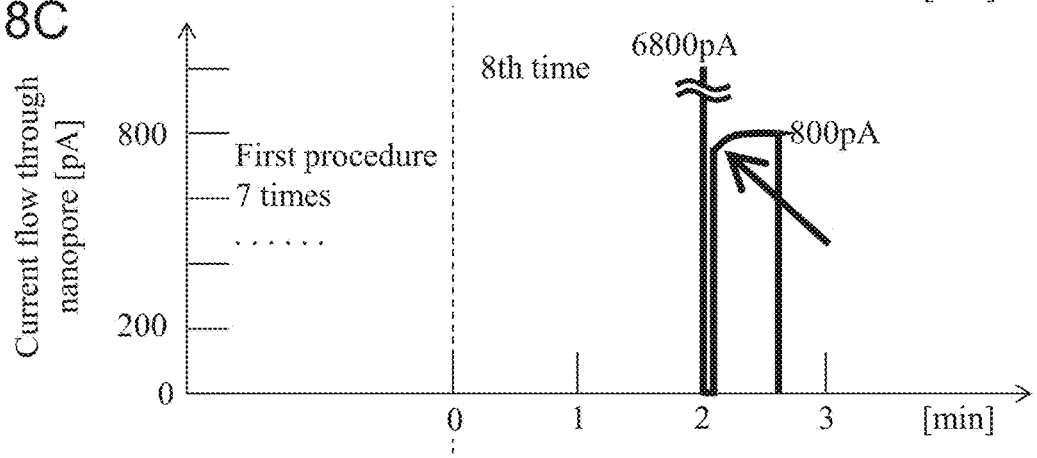

FIG. 18(a) illustrates a current change in a case where a hole with a diameter of 2 nm was formed in a membrane having a thickness of 10 nm. FIG. 18(b) illustrates a current change in a case where a hole having a diameter of 3 nm was formed in a membrane having a thickness of 10 nm. FIG. 18(c) illustrates a current change in a case where the hole opening processing load was increased and the hole opening was implemented with the target of forming a hole with a diameter of 4 nm in a membrane with a thickness of 20 nm.

When the current waveform in the step of measuring the hole diameter by applying the hole diameter measurement voltage after completion of hole opening was analyzed in detail, in FIG. 18(c) in particular, a behavior was confirmed in the graph in which the current value once dropped at the timing of application of the hole diameter measurement voltage, and then it stabilized at a constant value (indicated by an arrow in the figure). In FIG. 18(a) and FIG. 18(b), the voltage applied between the first electrode and the second electrode was 4 V and 5 V, respectively; in FIG. 18(c), a higher voltage of 8.5 V was applied because the membrane was thicker and the target hole diameter was greater. It is estimated that the waveform of the graph, in which the current value was once dropped and then stabilized, is probably due to the fact that, by the application of a higher voltage at the time of hole opening, a number of charges accumulated on the membrane material surface, and the accumulated charges were released at the moment the voltage was decreased to the voltage of 1 V for hole diameter measurement value.

Accordingly, in order to eliminate the estimated cause, i.e., the accumulation of surface charges, immediately after the hole opening under the condition of FIG. 18(c) (the hole opening voltage of 8.5 V, the hole diameter measurement voltage of 1 V), the condition was modified to apply an inverse voltage of −2 V for 5 seconds, followed by a transition to hole diameter measurement. As a result, at the time of application of the hole diameter measurement voltage of 1 V, the behavior of the current value once dropping in the graph and then stabilizing at a constant value was not observed anymore, and the current during the hole diameter measurement exhibited a constant value.

Figure 20:
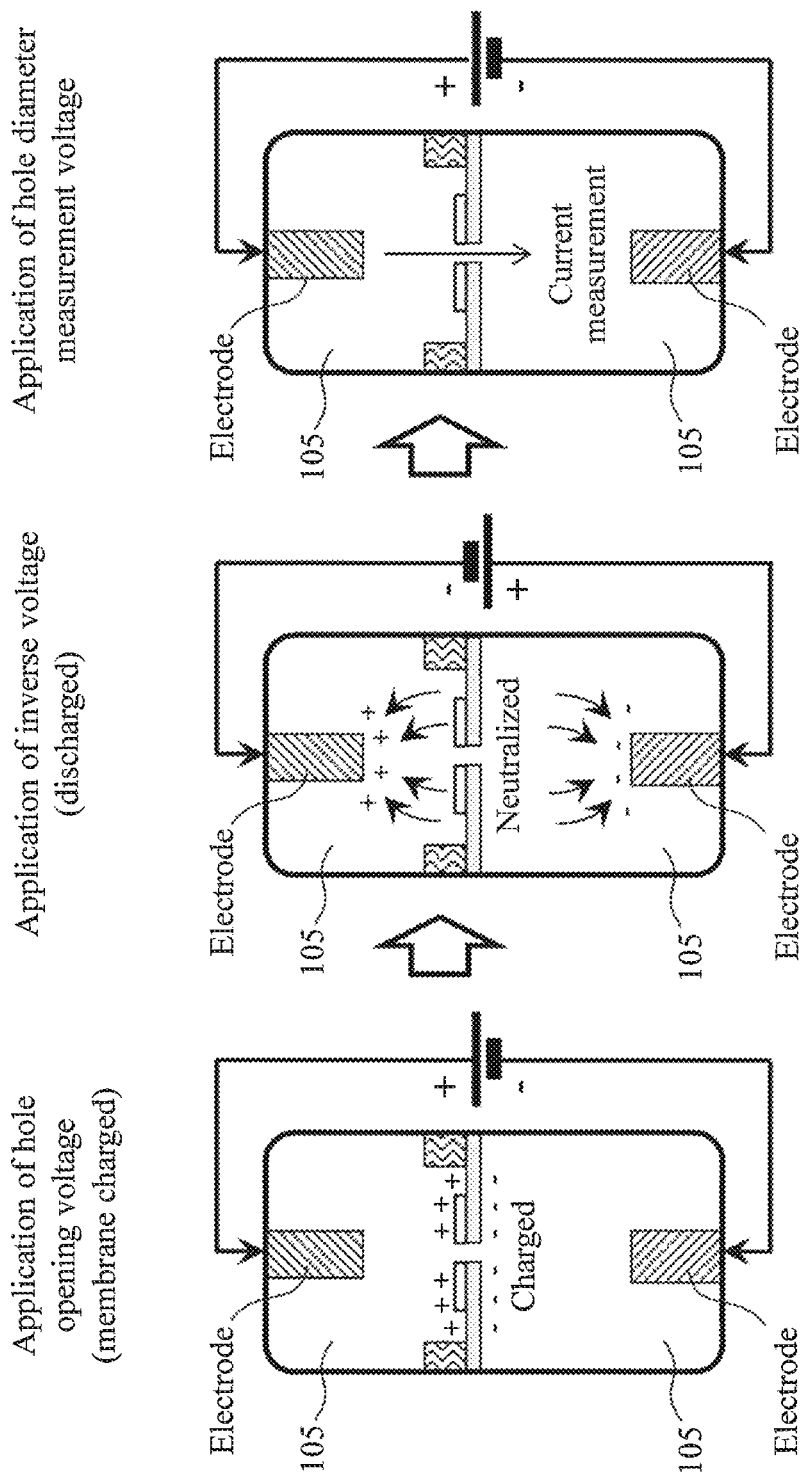
FIG. 20 illustrates an implementation example (reverse voltage application).

It is believed that by thus resetting the surface accumulated charges with an inverse voltage, in principle the hole diameter measurement accuracy can be increased and, as a result, the hole can be formed with a more precise diameter. The present experiment showed that the influence of surface charge accumulation was particularly pronounced when the voltage was increased to 8.5 V. However, because the surface charge accumulation is more or less possible, the process of applying an inverse voltage may preferably be inserted as a charge elimination step after the hole formation voltage application step. FIG. 20 illustrates how, in the presence of the influence of charges due to the hole opening voltage, the hole diameter measurement can be accurately performed by eliminating the surface accumulated charges through inverse voltage application.

Implementation Example 5

Figure 9:
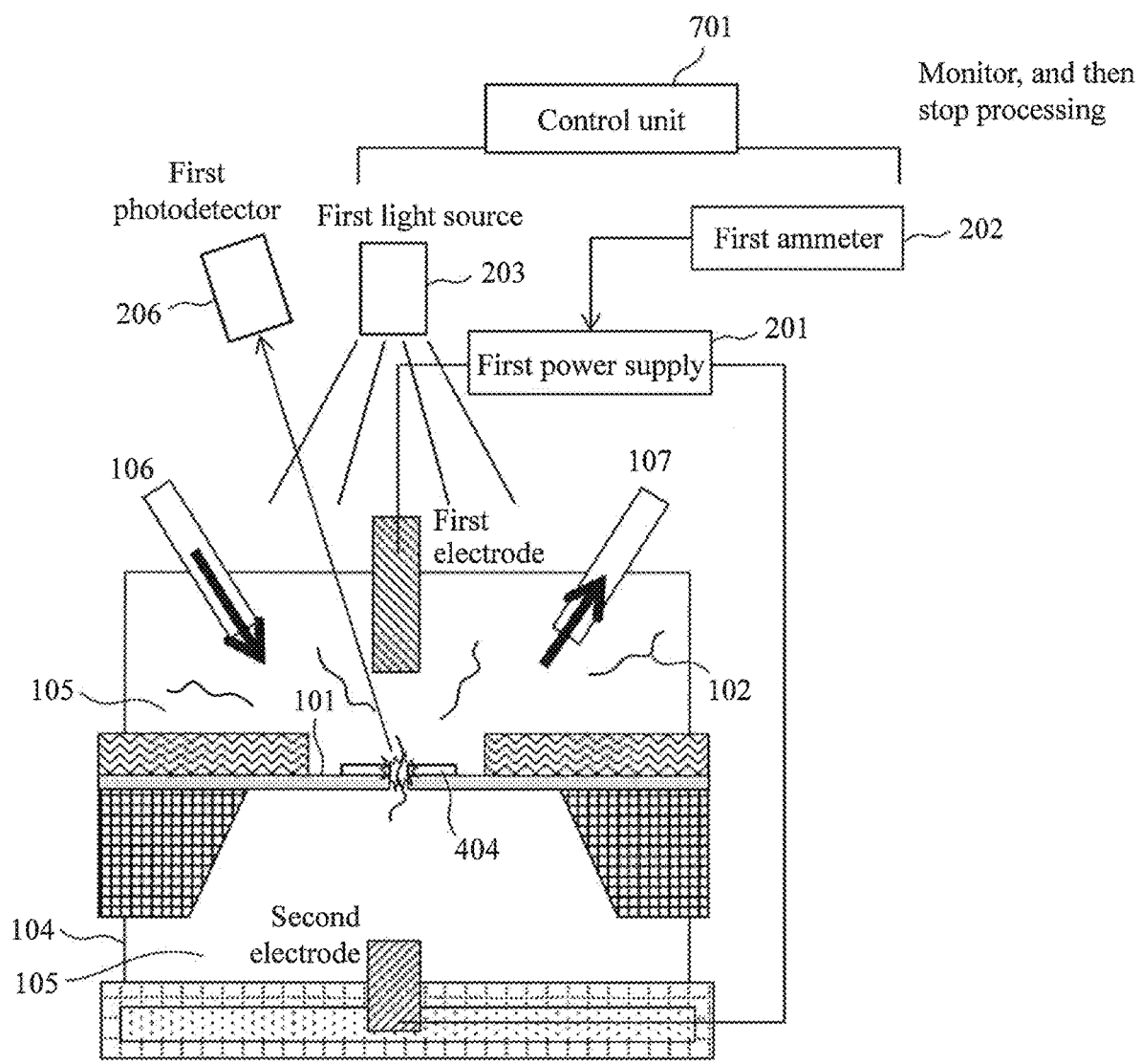
FIG. 9 describes an example of implementation of DNA measurement using a plasmon enhancement structure according to the present invention.

An example will be described in which a DNA molecule was measured using a nanopore device through the use of light. The overall configuration comprised a first light source 203 and a first photodetector 206, as illustrated in FIG. 9, where the bow-tie on the near-field light generating element 404 was irradiated with light from the light source, and light from the DNA molecule passing through the hole was measured by means of a detector.

For example, as illustrated in FIG. 11, in the chamber, there was loaded a chip in which, on a membrane with a thickness of 5 nm, 10×10, or a total of 100, elements including the bow-tie structures for the optical measurement system formed therein were formed in parallel, both sides of the chamber isolated by the membrane were filled with the KCl aqueous solution, and then the first electrode and the second electrode were set by being immersed in the KCl aqueous solution in either side of the chamber. Of the upper/lower regions isolated by the membrane, in the upper region, the first electrode was installed with respect to each of the 100 parallel elements, so that there were a total of 100 first electrodes. On the other hand, in the region below the membrane, there was one common electrode with respect to the 100 membranes because the second electrode may have a common potential. The 100 elements were irradiated with light, and a hole was formed by applying a voltage to each element by the above-described method. It is possible in principle to apply the voltage to all 100 of the elements simultaneously so as to form the holes simultaneously. In the present implementation example, however, the voltage was applied to one element after another sequentially using a switch 505 with which the 100 first electrodes for the 100 membranes had been individually provided, and 100 holes were formed at the respective bow-tie gap positions while the hole diameter was checked individually. Thereafter, without detaching the membrane chip from the chamber, an aqueous solution containing the DNA was put into the upper chamber as is, and then the process was transitioned to the DNA molecule measurement.

Figure 11A:
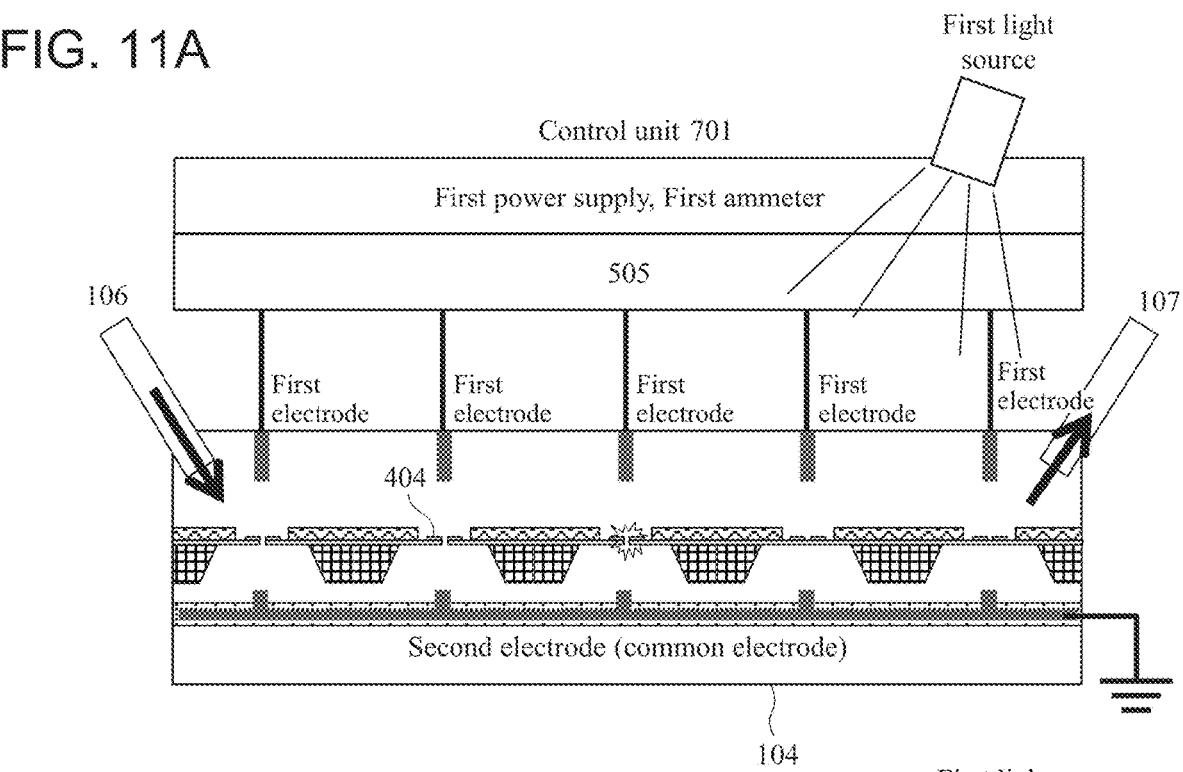
FIG. 11A illustrates an embodiment of hole opening in a multiple sensor array according to the present invention.
Figure 11B:
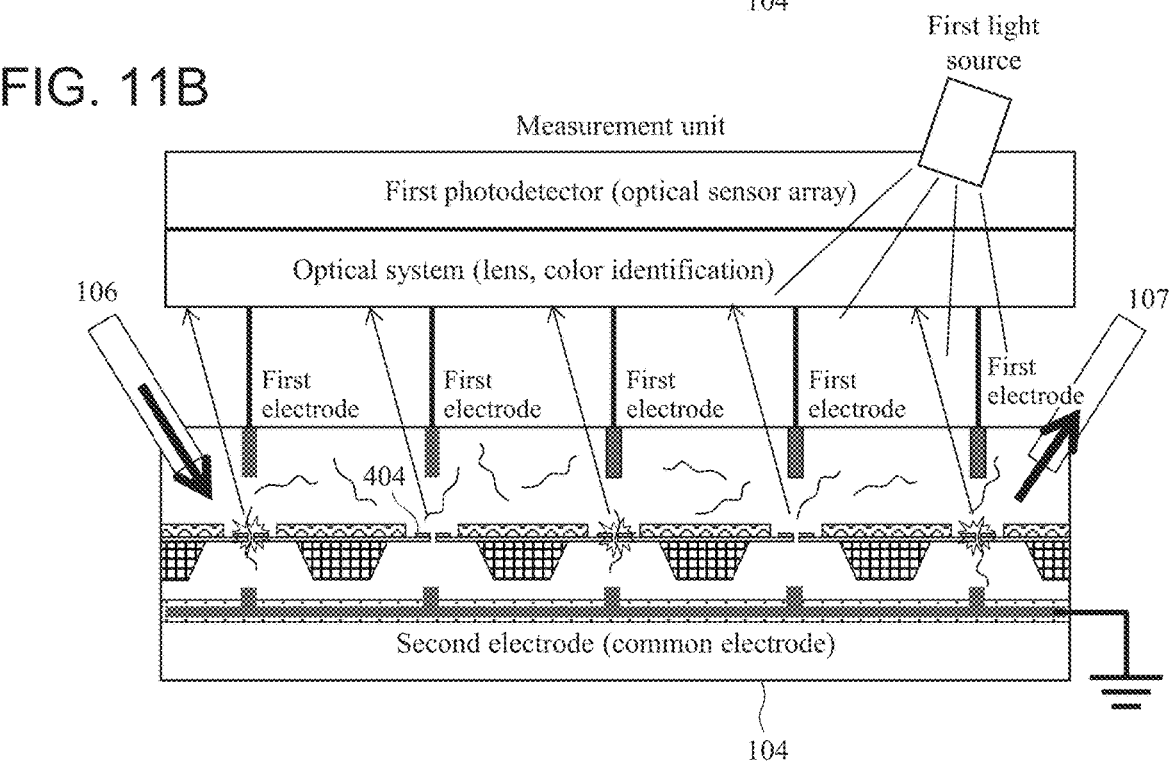
FIG. 11B illustrates an embodiment of measurement using the multiple sensor array according to the present invention.

As illustrated in. FIGS. 11(a) and 11(b), the bow-ties on the membrane were irradiated with light from the first light source so as to generate enhanced near-field light at the bow-tie gap, and the DNA molecule passing through the hole was excited. Because labeling dye was specifically added to each of the four types of bases of the DNA molecule, when the DNA molecule passed through the hole, fluorescence from each dye was observed with the first photodetector using a color filter as a spectroscopy means, indicating that a signal for analyzing the passing molecule had been obtained. The measurement according to the present implementation example was achieved for the first time by aligning the hole position at the position where the molecule was excited by the method described in the present description, and by forming the hole with a highly accurately controlled diameter. In the present evaluation, as the light for exciting the fluorescence dye for analyzing the four types of bases (A, G, C, T) of the DNA, mixed laser light of wavelengths 505 nm and 642 nm was used. This is one of conventional wavelength selections for causing all of four types of fluorescence to be emitted, as will be described below. Because the intensity of excitation light was enhanced by the plasmon enhancement device, in the current experiment, the laser output on the order of 50 mW was sufficient for both wavelength 505 nm and wavelength 642 nm, although the output may depend on the degree of enhancement. In principle, a non-coherent light source may be used instead of a laser, as long as the light source can output light of the same excitation wavelengths. In this case, while it may be possible to use various wavelengths by selecting the dye for the analysis of the four types of bases, in the present example, as the wavelength for analysis, 520 nm was used for A, 666 nm was used for G, 567 nm was used for C, and 702 nm was used for T.

Figure 22A:
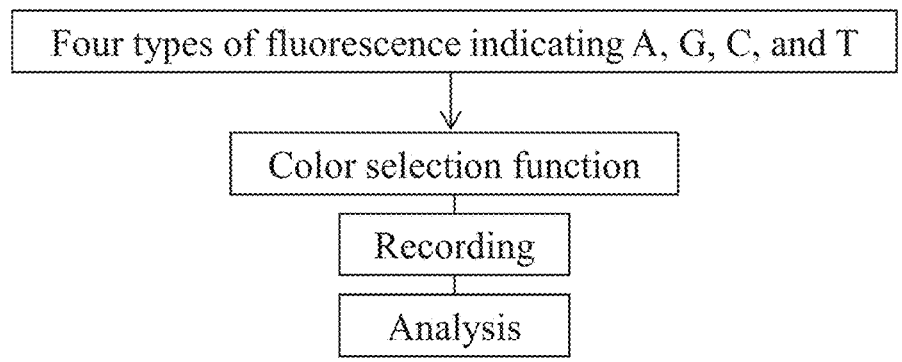
FIG. 22A describes an implementation example (DNA analysis).
Figure 22B:
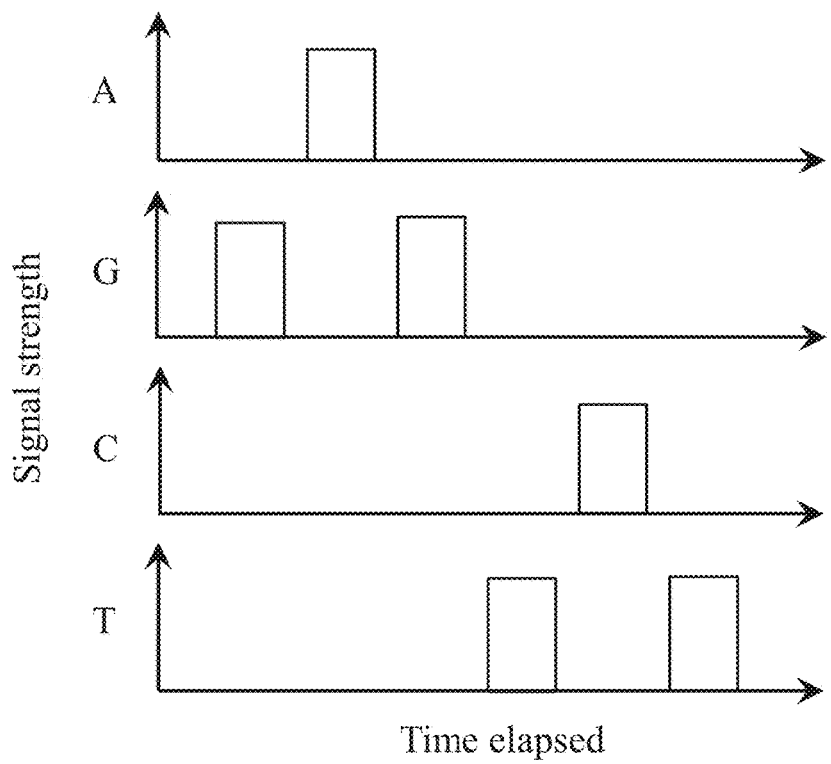
FIG. 22B describes the implementation example (DNA analysis results).

By constructing a system provided with the function for identifying the four types of light and configured to successively record the obtained light signals, such system can be used as a DNA sequencer. FIG. 22(a) illustrates a schematic block diagram of the system. FIG. 22(b) illustrates signals analyzed using a color filter plate in the color selection function. portion, for example. The color identification function may be a spectroscopy unit using a prism or a diffraction grating, as long as the four types can be identified. In the example of FIG. 22(b), the result obtained was G, A, G, T, C, and T.

A number of such pieces of data/information were gathered, and computing, such as an estimation based on overlapping features or a superposition of plurality of data items, was performed by an analysis unit, whereby the original order of arrangement of the four types of bases was able to be clarified from the connection of analyzed pieces, thus making it possible to configure and confirm the basic function as a DNA sequencer.

The optical measurement method may include Raman spectroscopy as a method that does not use labeling dye. The four types of bases of a DNA molecule, even when excited by the same wavelength of light, each emit Raman light of different wavelengths because their energy levels in excited state differ depending on the difference in molecule structure. Accordingly, measurement was also attempted with respect to a DNA molecule to which no labeling dye was added with respect to the four types of bases. Using the first photodetector provided with a diffraction grating spectroscope as the spectroscopy means, it was possible to observe Raman light in accordance with the specific wavelength of each of the four types of bases. In this evaluation, for Raman spectroscopic evaluation, laser light of 638 nm or 785 nm was used as the light for exciting the four types of bases in the DNA (A, G, C, T). At either wavelength, a Raman spectrum in which the four types of bases were separated, as will be described below, was obtained. As in the case of fluorescence dye, the intensity of excitation light was enhanced by the plasmon enhancement device, so that the laser output on the order of 50 mW was sufficient. Note, however, that, because Raman spectroscopy requires high-resolution identification, it is preferable to use laser so as to achieve excitation at a sharp single wavelength. From the four types of bases, peaks with slight wavelength differences (in terms of energy value, peaks with differences on the order of several 100 $cm^{-1}$ at most) are obtained. When the molecular structure is different, the vibration spectrum structure is different, which appears as a peak wavelength difference in the spectrum in the wavelength range observed by Raman spectroscopy. This is referred to as a Raman shift in the field of Raman spectroscopy. Specifically, because the four types of bases each have a different Raman shift, this appears as the separate peaks enabling identification of the four types of bases on the Raman spectrum.

Figure 23A:
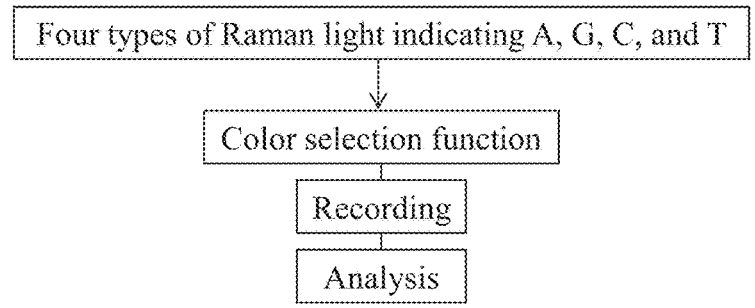
FIG. 23A describes an implementation example (DNA analysis).
Figure 23B:
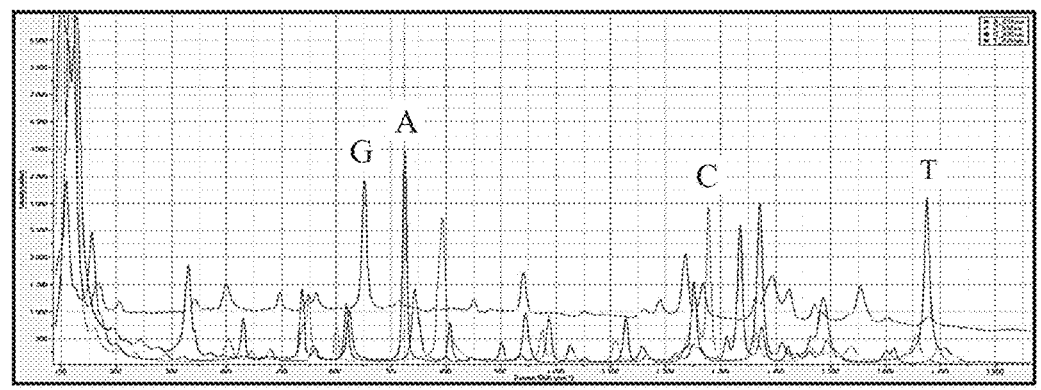
FIG. 23B describes an implementation example (Raman spectrum).
Figure 23C:
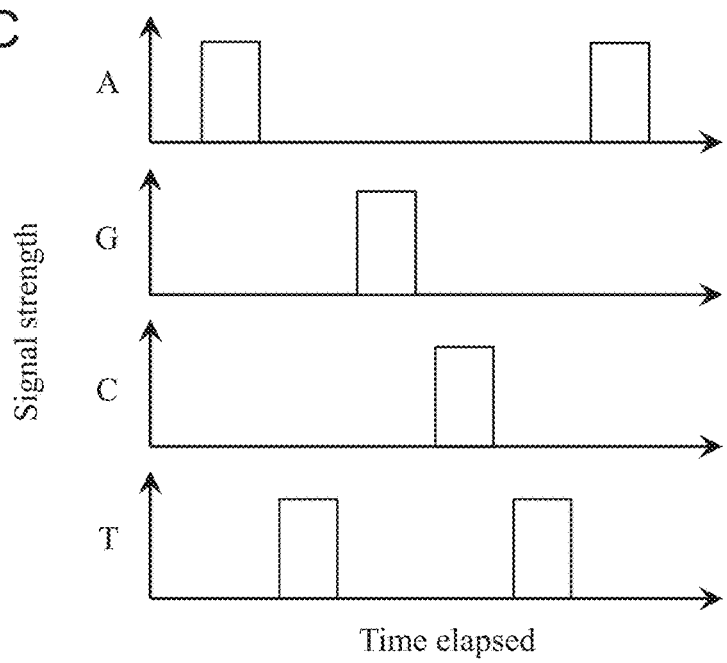
FIG. 23C describes an implementation example (DNA analysis results).

By constructing a system provided with the function for identifying the four types of light (light with different wavelengths due to different Raman shift), and for successively recording the obtained light signals, such system can be used as a DNA sequencer, as in the case of the fluorescence system. FIG. 23(a) illustrates a schematic block diagram for the case where Raman spectroscopy is used. FIG. 23(b) illustrates an example of a spectrum obtained when excitation was caused at the wavelength of 638 nm, using, in the color selection function portion, a diffraction grating spectroscope and an optical system that focused an observation point (which may be generally referred to as a Raman microscope). As the peak wavelengths were thus separated, an attempt was made to analyze DNA using the four peaks, of which the result is shown in FIG. 23(c). In the example of FIG. 23(c), the result obtained was A, T, G, C, T, and A.

Such data/information was gathered, and computing, such as an estimation from overlapping features or a superposition of a plurality of data items, was performed by an analysis unit, whereby the original order of arrangement of the four types of bases was able to be clarified from the connection of the analyzed pieces, thus making it possible to configure and confirm the basic function as a DNA sequencer.

Implementation Example 6

An example will be described in which a DNA molecule was measured based on a blocking current, using a nanopore device. The overall configuration was such that, of the configuration of FIG. 9, the first light source 203 and the first photodetector 206 were not used, and a change in current when the DNA molecule passed was measured, while monitoring, using a first ammeter 202, the current that flowed through the nanopore when a voltage was applied to the electrodes above and below the membrane. This is a method whereby the difference in a blocking rate of blocking of the nanopore by the DNA molecule is measured, and the type of the base that has passed is identified. For example, the following description is based on a configuration in which, of the configuration of FIG. 11, the first light source 203, the photodetector 206, and associated optical systems (lens, color identification) were not used.

In the chamber, there was loaded a chip in which, on a membrane with a thickness of 5 nm, 10×10, or a total of 100, elements having the bow-tie structures for the optical measurement system formed therein were formed in parallel; both sides of the chamber isolated by the membrane were filled with the KCl aqueous solution; and then the first electrode and the second electrode were respectively set by being immersed in the KCl aqueous solution in either side of the chamber. Of the upper/lower regions isolated by the membrane, in the upper region, a total of 100 first electrodes were installed, one for each of the 100 parallel elements. On the other hand, in the region below the membrane, one common electrode was provided with respect to the 100 membranes, for the second electrode may have a common potential. The 100 elements were irradiated with light, and a hole of 2 nm was formed in each element by applying a voltage by the above-described method. Using a switch provided individually for the 100 first electrodes with respect to the 100 membranes, the voltage was applied to one element after another sequentially, while the hole diameter was checked individually, whereby 100 holes were formed at the respective bow-tie gap positions. Thereafter, without detaching the membrane chip from the chamber, an aqueous solution containing DNA was put into the upper chamber as is, and the process was transitioned to DNA molecule measurement.

In the present implementation example, the measurement of the DNA molecule by optical measurement was not performed. Instead, the amount of decrease in the current that flowed through the hole due to blocking of the hole as the molecule passed through the hole was measured (blocking current system). Initially, with the first light source being turned OFF, a voltage was applied to the first electrode and the second electrode using the first power supply, and an ion current passing through the hole was continuously monitored using an ammeter attached to the first power supply. As a result, a decrease in characteristic ion current (blocking) was observed when the DNA molecule passed through the hole, thus making it possible to observe the passage of the DNA molecule in the aqueous solution through the hole.

Implementation Example 7

Figure 10:
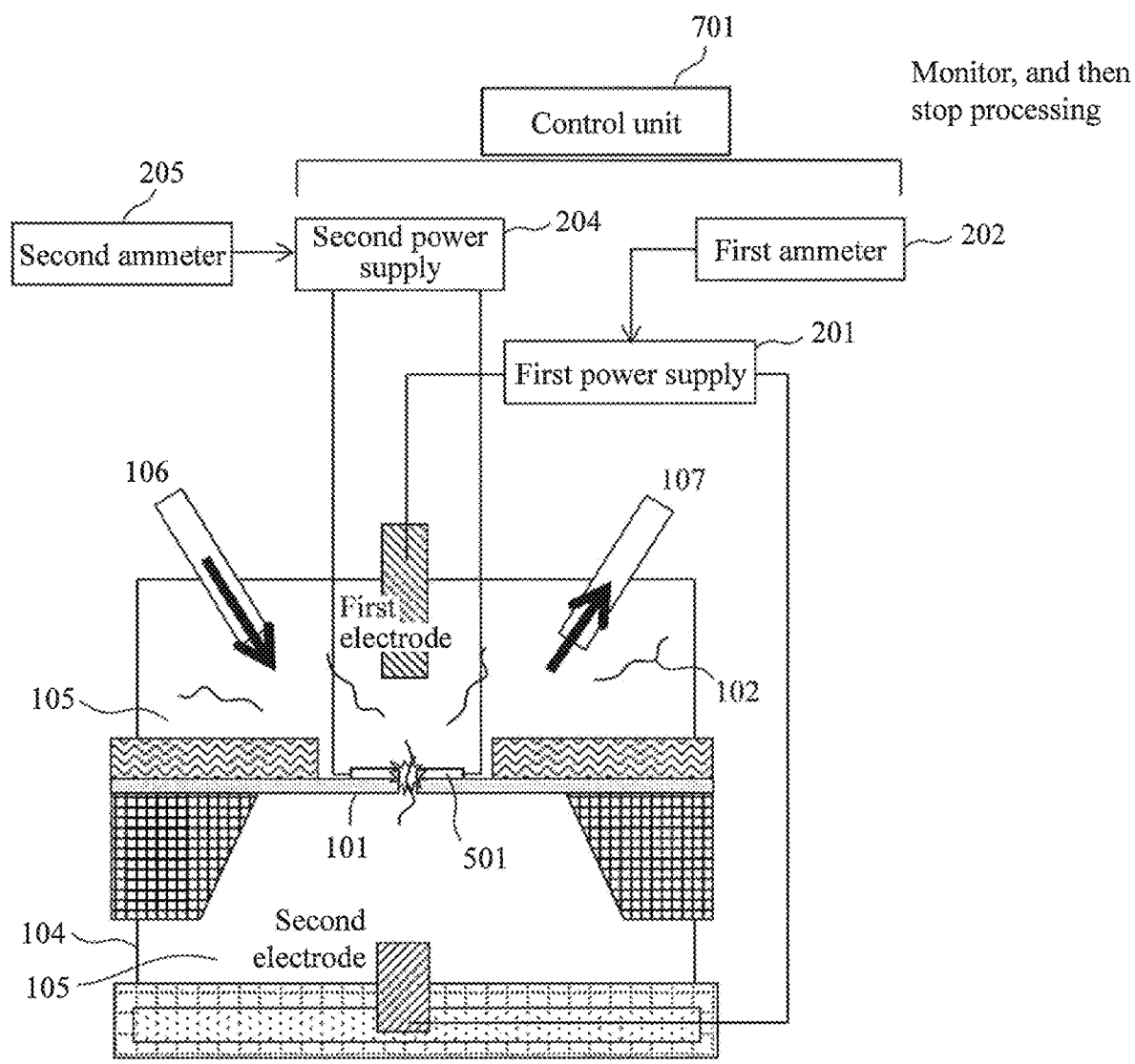
FIG. 10 describes an example of implementation of DNA measurement using a pair of tunnel current measuring electrodes according to the present invention.

An example will be described in which a DNA molecule was measured through a tunnel current using a nanopore device. The overall configuration was such that, as illustrated in FIG. 10, a current that flowed as the DNA molecule passed through the hole was measured, using a tunnel current measurement electrode 501.

This is a method whereby, when the DNA molecule passes through the nanopore, the tunnel current that flows through each base is measured so as to identify the type of the base that has passed, depending on a difference in the current. For example, as illustrated in FIG. 21, in the chamber, there was loaded a chip in which 10×10, or a total of 100, elements having tunnel current measurement electrode pairs formed therein were formed in parallel on a membrane having a thickness of 5 nm, both sides of the chamber isolated by the membrane were filled with the KCl aqueous solution, and then the first electrode and the second electrode were set by being immersed in the KCl aqueous solution in either side of the chamber. Of the upper/lower regions isolated by the membrane, in the upper region, a total of 100 first electrodes were installed, one for each of the 100 parallel elements. On the other hand, in the region below the membrane, one common second electrode was provided for the 100 membranes. A voltage was applied to the tunnel current measurement electrode pairs of the 100 elements, using the second power supply, so as to excite the gaps of the electrode pairs, and a hole was formed by applying a voltage to each element by the above-described method, using the first power supply. It is possible in principle to apply the voltage to all 100 elements simultaneously so as to form the holes simultaneously. However, in the present implementation example, using a switch 505 provided individually for the 100 first electrodes with respect to the 100 membranes, the voltage was applied to one element after another sequentially, and the 100 holes were formed at the gap positions of the respective electrode pairs while the hole diameter was checked individually. Thereafter, without detaching the membrane chip from the chamber, an aqueous solution containing DNA was put into the upper chamber as is, and then the process was transitioned to DNA molecule measurement.

Figure 21A:
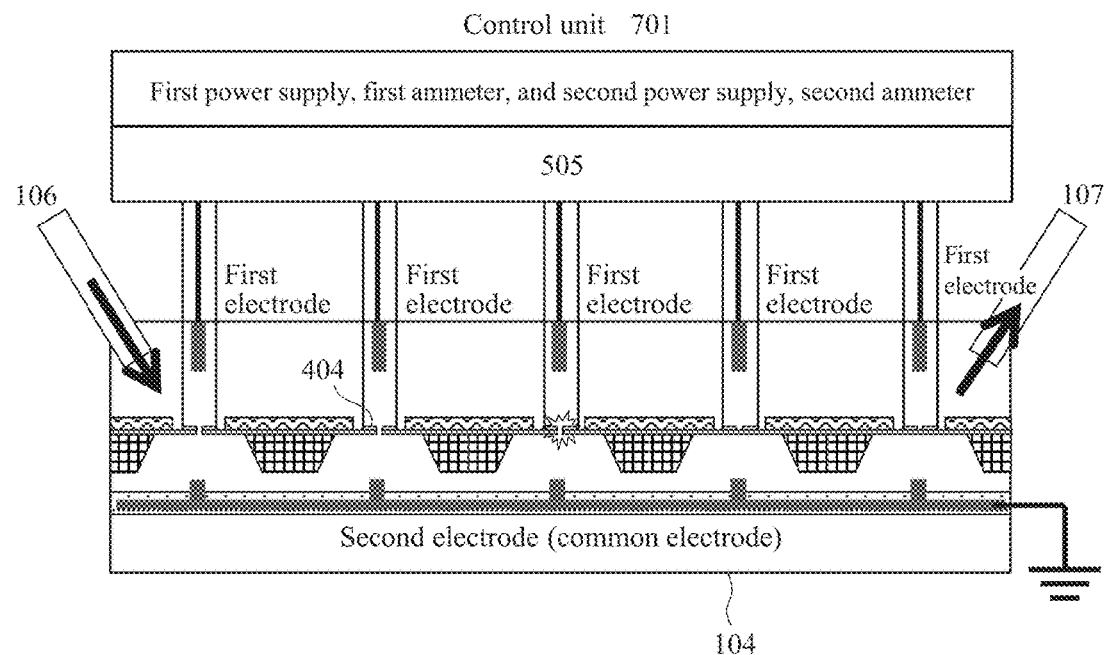
FIG. 21A illustrates an embodiment of hole opening in a multiple sensor array according to the present invention.
Figure 21B:
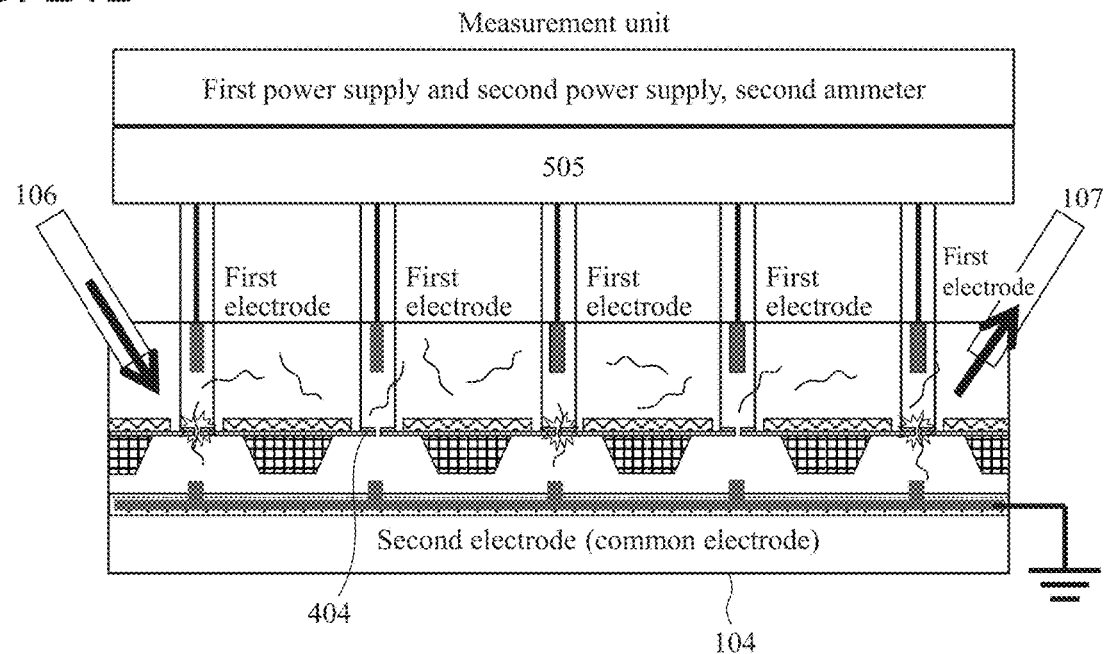
FIG. 21B illustrates an embodiment of measurement using the multiple sensor array according to the present invention.

As illustrated in FIGS. 21(a) and 21(b), a voltage was applied to the electrode pairs on the membranes, using the second power supply, and a tunnel current that flowed through each base was measured as the DNA molecule passed through the hole. The difference in the flow of tunnel current due to the difference in the molecule structure of the four types of bases of the DNA molecule was able to be observed, thus indicating that the method can be used to obtain a DNA base sequence. The measurement according to the present implementation example was achieved for the first time by aligning the hole position at a position exactly aligned with the electrode pair gap such that a tunnel current can be caused to flow through the molecule by the method described in the present description, and by forming the hole with a highly accurately controlled hole diameter.

Implementation Example 8

The nanopore formation methods using the techniques according to Implementation Examples 1 to 7 were implemented with respect to: inorganic material membranes other than the $Si_3N_4$ membrane, such as a SiON membrane, a $SiO_2$ membrane, an alumina membrane, a $HfO_2$ membrane, a HfSiON membrane, a $TiO_2$ membrane, a zirconium membrane, a $ZrSiO_4$ membrane, and a yttria membrane; and other polymer films and the like. While the voltage necessary for hole opening may differ from one material to another due to differences in material characteristics such as bandgap, it was confirmed that basically the present technology can be applied for the above-described materials.

As to the light source, a common light source may be used for generating near-field light and for DNA analysis by optical measurement, as long as its power or wavelength can be varied to suit the measurement.

REFERENCE SIGNS LIST

101 Thin-film membrane region
102 DNA molecule

103 Nanopore
104 Chamber
105 Aqueous solution
106 Aqueous solution inlet port
107 Aqueous solution outlet port
108 Light excitation
109 Light signal
110 Electrical signal
201 First power supply
202 First ammeter
203 Light source
204 Second power supply
205 Second ammeter
206 Photodetector
401 Insulating film membrane
402 Conductor thin-film
403 Hole
404 Bow-tie
405 Gap
406 Conductor dot
407 Insulator thin-film between upper and lower conductor dots
408 Near-field light generated position
501 Electrode pair
502 Gap between electrode pair
503 Electric wiring
504 Current generated position
505 Select switch
701 Control unit

The invention claimed is:

1. A method for forming a hole with respect to a film, the method comprising:

a first step of, while an insulating film having a near-field light generating element placed thereon is being irradiated with light in an electrolytic solution, or after the film was irradiated with light in the electrolytic solution, or after the film that has been irradiated with light is disposed in the electrolytic solution, applying a first voltage between a first electrode and a second electrode that are installed in the electrolytic solution across the film, wherein the near-field light generating element is configured to generate a near-field light and to reduce an energy required for causing dielectric breakdown of the film at a position where the near-field light is generated, the first voltage is a voltage that causes dielectric breakdown and creates the hole, and the irradiated light is a light that causes electron excitation; and a second step of, after the first step, applying a second voltage which is smaller than the first voltage between the first electrode and the second electrode, and detecting a value of a current that flows between the first electrode and the second electrode due to the application of the second voltage;

a procedure of repeating the first step and the second step is stopped when the current value reaches or exceeds a pre-set threshold value, which is related to a relationship between a diameter of a hole formed and the current value, and determining that a size of the hole was properly formed when, during the second step, the current associated with the second voltage is stable.

2. The hole formation method according to claim 1, wherein the procedure is performed such that the first voltage becomes greater or the time of application of the first voltage becomes longer in an m-th repetition than in an n-th repetition (where n<m).

3. The hole formation method according to claim 1, further comprising a step of applying a voltage of an inverse polarity from the first voltage between the first step and the second step.

* * * * *